US012738379B2

(12) United States Patent
Karsikas et al.

(10) Patent No.: US 12,738,379 B2
(45) Date of Patent: Sep. 15, 2026

(54) TECHNIQUES FOR BIOFEEDBACK USING HEART RATE DATA

(71) Applicant: Oura Health Oy, Oulu (FI)

(72) Inventors: Mari Pauliina Karsikas, Oulu (FI); Janne Käki, Oulu (FI); Samuli Hietala, Oulu (FI); Heli Tuulia Koskimäki, Oulu (FI); Olli Petteri Heikkinen, Oulu (FI); Tuomas Viljami Kenttä, Liminka (FI)

(73) Assignee: Oura Health Oy, Oulu (FI)

( * ) Notice: Subject to any disclaimer, the term of this patent is extended or adjusted under 35 U.S.C. 154(b) by 525 days.

(21) Appl. No.: 18/068,357

(22) Filed: Dec. 19, 2022

(65) Prior Publication Data

US 2024/0203586 A1 Jun. 20, 2024

(51) Int. Cl.

| | |
|---|---|
| ***A61B 5/00*** | (2006.01) |
| ***A61B 5/024*** | (2006.01) |
| ***G16H 50/20*** | (2018.01) |

(52) U.S. Cl.

CPC ............ *G16H 50/20* (2018.01); *A61B 5/002* (2013.01); *A61B 5/02438* (2013.01); *A61B 5/486* (2013.01); *A61B 5/6802* (2013.01); *A61B 5/7267* (2013.01)

(58) Field of Classification Search

CPC ........ G16H 50/20; G16H 50/30; G16H 40/60; A61B 5/02438; A61B 5/6802; A61B 5/002; A61B 5/486; A61B 5/7267

See application file for complete search history.

(56) References Cited

U.S. PATENT DOCUMENTS

| | | | |
|---|---|---|---|
| 11,446,466 B1 * | 9/2022 | Shvartzman | A61B 5/4809 |
| 2016/0246326 A1 * | 8/2016 | von Badinski | A61B 5/6826 |
| 2019/0163270 A1 * | 5/2019 | Da Silva | A61B 5/486 |
| 2021/0085245 A1 * | 3/2021 | Cihan | A61B 5/4884 |
| 2021/0204867 A1 | 7/2021 | Toth et al. | |
| 2022/0032162 A1 | 2/2022 | Putnam | |
| 2022/0071570 A1 * | 3/2022 | Cox | A61B 5/02405 |
| 2022/0076666 A1 | 3/2022 | Trehan | |
| 2022/0117837 A1 | 4/2022 | Northen et al. | |
| 2022/0280105 A1 * | 9/2022 | Dixit | A61B 5/02405 |

FOREIGN PATENT DOCUMENTS

| | | |
|---|---|---|
| CN | 102449560 A | 5/2012 |
| CN | 103154954 A | 6/2013 |
| KR | 20150099430 A1 | 8/2015 |

OTHER PUBLICATIONS

International Search Report and Written Opinion—PCT/US2023/083618—ISA/EPO—Apr. 16, 2024.

* cited by examiner

*Primary Examiner* — Catherine M Voorhees
(74) *Attorney, Agent, or Firm* — ArentFox Schiff LLP

(57) ABSTRACT

Methods, systems, and devices for biofeedback are described. A user device may acquire physiological data associated with a user from a wearable device. The user device may select a feedback response that may include one or more of audio, haptic, or visible light feedback. The user device may determine parameters for the feedback response. The parameters may include one or more of a magnitude, a duration, or a frequency, associated with one or more of the audio, haptic, or visible light feedback. The user device or the wearable device may output the feedback response indicative for regulating the physiological data associated with the user.

20 Claims, 11 Drawing Sheets

400

500

TECHNIQUES FOR BIOFEEDBACK USING HEART RATE DATA

FIELD OF TECHNOLOGY

The following relates to wearable devices and data processing, including techniques for biofeedback (also referred to as "biofeedback response" or "response") using heart rate data.

BACKGROUND

Some wearable devices may be configured to collect data from users associated with heart rate. For example, some wearable devices may be configured to collect heart rate data from a user while the user is engaged in an activity and provide insights relevant to the user. These devices may provide insights using post-activity analysis and provide insights relevant to the activity.

DETAILED DESCRIPTION

Figure 1:
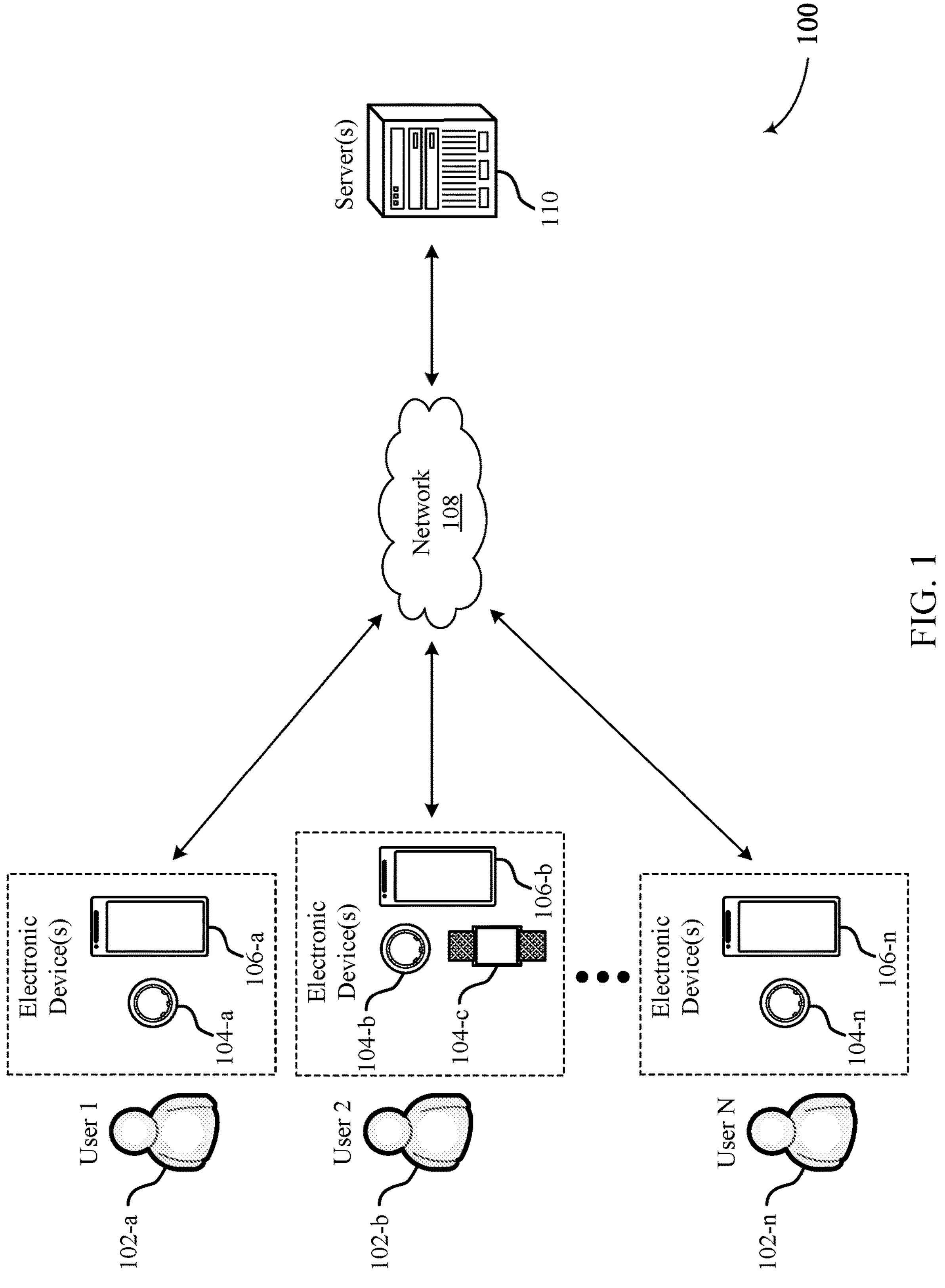
FIG. 1 illustrates an example of a system that supports techniques for biofeedback using heart rate data in accordance with aspects of the present disclosure.

Various applications may collect information associated with a user to provide insights relevant to the user. An application associated with health and wellness tracking may include activity content, physiological content, and the like. For example, a wellness application may include information associated with a user's activity history, the user's physiological history relevant to the user's activity history, and the like. However, this application for providing insights to a user based on their activity history, physiological history, or the like may be insufficient in providing insights that are most effective in causing one or more physiological responses for a particular person.

A system including a wearable device and a user device may acquire physiological data, and based on the acquired physiological data, may provide insights relevant to the user. The system may select a feedback response (e.g., a biofeedback response) indicative of the physiological data associated with the user. The feedback response may include one or more of audio feedback (e.g., audio pulses, or the like), haptic feedback (e.g., tactile vibration pulses, or the like), or visible light feedback (e.g., visible light pulses, or the like). In some implementations, the system may determine one or more parameters for the feedback response based at least in part on the physiological data. The one or more parameters may include one or more of a magnitude, a duration, or a frequency, associated with one or more of the audio feedback, the haptic feedback, or the visible light feedback. Other examples of the one or more parameters include a volume of the audio feedback (e.g., audio pulses), a brightness of the visible light feedback (e.g., visible light pulses), etc.

The system may cause a user device to output the feedback response indicative of the physiological data in accordance with the one or more parameters for the feedback response. The feedback response may be indicative to the user for regulating (e.g., maintaining, adjusting, switching, increasing, decreasing, and the like) a heart rate of the user. For example, the feedback response may indicate to the user, to maintain a heart rate of the user at a current level (e.g., a current beats per minute), using one or more of the audio feedback (e.g., audio pulses), the haptic feedback (e.g., tactile vibration pulses), or the visible light feedback (e.g., visible light pulses). Alternatively, the feedback response may indicate to the user, to adjust (e.g., increase or decrease) a heart rate of the user from a current level, using one or more of the audio feedback, haptic feedback, or visible light feedback.

As a result, the system facilitates improvements to the user's general wellness by providing a biofeedback according to the user's physiological data and using audio feedback, haptic feedback, or visible light feedback. While much of the present disclosure is described in the context of physiological data, this is not to be regarded as a limitation of the present disclosure. In particular, techniques described herein may enable providing biofeedback to a user that may help improve the user's physiological data. Moreover, physiological data associated with a user may be used to update any score, measure, metric, or other abstraction associated with a user's health, mental wellness, or activity. Additionally, while much of the present disclosure is described in the context of audio pulses, tactile vibration pules, and visible light pulses, these are not to be regarded as a limitation of the present disclosure.

Aspects of the disclosure are initially described in the context of systems supporting physiological data collection from users via wearable devices. Aspects of the disclosure are further illustrated by and described with reference to apparatus diagrams, system diagrams, and flowcharts that relate to techniques for biofeedback using heart rate data.

FIG. 1 illustrates an example of a system 100 that supports techniques for biofeedback using heart rate data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for biofeedback. In particular, the system 100 illustrated in FIG. 1 may support techniques for providing insights to a user 102 by causing a user device 106 corresponding to the user 102 to display insights relevant to the user 102 according to physiological data associated with the user 102. For example, as shown in FIG. 1, a user 102-*a* may be associated with a wearable device 104-*a* (e.g., ring 104-*a*) and a user device 106-*a*. The user device 106-*a* may acquire physiological data associated with the user 102-*a* from the wearable device 104-*a*. The physiological data may include at least heart rate data associated with the user 102-*a*. The user device 106-*a* may select a feedback response indicative of the physiological data associated with the user 102-*a*. The feedback response may include one or more of audio pulses, tactile vibration pulses, or visible light pulses.

The system 100 may provide insights to the user 102-*a* associated with the physiological data of the user 102-*a* using one or more of audio pulses, tactile vibration pulses, or visible light pulses. Put another way, the system 100 may output to the user 102-*a*, a representation of a heart rate of the user 102-*a* in the form of audio pulses, tactile vibration pulses, or visible light pulses. For example, the user device 106-*a* may output a heart rate of the user 102-*a* in the form of one or more metronome audio pulses corresponding to the heart rate of the user 102-*a*. In some implementations, the user device 106-*a* may output a modified version of the heart rate of the user 102-*a*. For example, the user device 106-*a* may output fewer metronome audio pulses (e.g., reduced heart beats per minute) of the heart rate of the user 102-*a*. Additionally or alternatively, the user device 106-*a* may output a modified version of the heart rate of the user 102-*a* in the form of modified tactile vibration pulses and/or visible light pulses as described herein. Although the above examples are described in context of audio pulses, the same or similar implementation's may be realized for tactile vibration pulses and/or visible light pulses. Any of the components of the system 100, including the wearable device 104-*a*, the user device 106-*a* associated with the user 102-*a*, the one or more servers 110, or any combination thereof, may output a heart rate of the user 102-*a* in the form of audio pulses, tactile vibration pulses, or visible light pulses.

The user device 106-*a* may determine one or more parameters for the feedback response based at least in part on the physiological data associated with the user 102-*a*. The one or more parameters may include a magnitude of the tactile vibration pulses, a volume of the audio pulses, a duration of each tactile vibration pulse, a duration of each audio pulse, a frequency of the tactile vibration pulses, a frequency of the audio pulses, a duration of each visible light pulse, a brightness of the visible light pulses, or a combination thereof. In accordance with the one or more parameters for the feedback response, the user device 106-*a* may output the feedback response indicative of the physiological data associated with the user 102-*a*. The feedback response may be indicative to the user 102-*a* for regulating (e.g., maintain, adjusting, switching, increasing, decreasing, and the like) one or more of the physiological data associated with the user 102-*a*. For example, the feedback response may indicate to the user 102-*a* to maintain a heart rate of the user 102-*a*. Alternatively, the feedback response may indicate to the user 102-*a* to adjust (e.g., increase or decrease) a heart rate of the user 102-*a*. The user device 106-*a* or any of the components of the system 100 may generate one or more of the audio pulses, the tactile vibration pulses, or the visible light pulses based at least in part on the heart rate data associated with the user.

In some implementations, any of the components of the system 100, including the wearable device 104-*a*, the user device 106-*a* associated with the user 102-*a*, the one or more servers 110, or any combination thereof, may determine an activity (e.g., a physical activity) the user 102-*a* is engaged in based at least in part on sensor data from the wearable device 104-*a*. Based on the determination, any of the components of the system 100, including the wearable device 104-*a*, the user device 106-*a* associated with the user 102-*a*, the one or more servers 110, or any combination thereof, may select the feedback response, determine the one or more parameters for the feedback response, or both, based at least in part on the activity the user 102-*a* is engaged in. In some implementations, any of the components of the system 100, including the wearable device 104-*a*, the user device 106-*a* associated with the user 102-*a*, the one or more servers 110, or any combination thereof, may output to the user 102-*a*, a representation of a heart rate of the user 102-*a* in the form of audio pulses, tactile vibration pulses, or visible light pulses based at least in part on the activity the user 102-*a* is engaged in. For example, the system 100 may output to the user 102-*a*, a representation of a heart rate of the user 102-*a* in the form of audio pulses, tactile vibration pulses, or visible light pulses based at least in part on a running cadence associated with the user 102-*a*.

In some implementations, the system 100 may, before the user 102-*a* engages in the activity, output audio pulses, tactile vibration pulses, or visible light pulses that may correspond to a pace and/or a speed (e.g., a walking pace, a walking speed, a running pace, a running speed, and the like) of the user 102-*a*. The audio pulses, tactile vibration pulses, or visible light pulses may be updated during the activity the user 102-*a* is engaged in, for example, based on a current heart rate of the user 102-*a*. In some implementations, the system 100 may incorporate biofeedback (e.g., the user's 102-*a* heart rate to music) to a song. For example, the system 100 may use the user's 102-*a* heart rate to control a selection of a song that has a certain base rhythm and the system 100 could time the user's running cadence to the certain base rhythm. In other implementations, the user 102-*a* may indicate the activity the user 102-*a* is engaged in, for example, via an application running on the user device 106-*a*.

In some other implementations, any of the components of the system 100, including the wearable device 104-*a*, the user device 106-*a* associated with the user 102-*a*, the one or more servers 110, or any combination thereof, may identify a Readiness Score or a Sleep Score associated with the user 102-*a*. Any of the components of the system 100, including the wearable device 104-*a*, the user device 106-*a* associated with the user 102-*a*, the one or more servers 110, or any combination thereof, may then select feedback response, determine the one or more parameters for the feedback response, or both, based at least in part on the Readiness Score or the Sleep Score associated with the user 102-*a*.

In other implementations, any of the components of the system 100, including the wearable device 104-*a*, the user device 106-*a* associated with the user 102-*a*, the one or more servers 110, or any combination thereof, may determine a change in one or more physiological data associated with the user 102-*a* after outputting the feedback response indicative of the physiological data to the user 102-*a*. For example, any of the components of the system 100, including the wearable device 104-*a*, the user device 106-*a* associated with the user

102-*a*, the one or more servers 110, or any combination thereof, may determine that the user's 102-*a* heart rate is lower or higher. Any of the components of the system 100, including the wearable device 104-*a*, the user device 106-*a* associated with the user 102-*a*, the one or more servers 110, or any combination thereof, may then adjust the feedback response including the one or more parameters for the feedback response based at least in part on the change in the one or more physiological data associated with the user 102-*a*. The user device 106-*a* associated with the user 102-*a* may output the adjusted feedback response indicative of the change in the one or more physiological data in accordance with the one or more adjusted parameters for the feedback response. For example, the user device 106-*a* may increase or decrease one or more of a magnitude of the tactile vibration pulses, a volume of the audio pulses, a duration of each tactile vibration pulse of the tactile vibration pulses, a duration of each audio pulse of the audio pulses, a frequency of the tactile vibration pulses, a frequency of the audio pulses, a duration of each visible light pulse of the visible light pulses, a brightness of the visible light pulses, or a combination thereof.

Additionally or alternatively, any of the components of the system 100, including the wearable device 104-*a*, the user device 106-*a* associated with the user 102-*a*, the one or more servers 110, or any combination thereof, may determine change in an activity the user 102-*a* is engaged in based at least in part on sensor data from the wearable device 104-*a*. Any of the components of the system 100, including the wearable device 104-*a*, the user device 106-*a* associated with the user 102-*a*, the one or more servers 110, or any combination thereof, may adjust the feedback response including the one or more parameters for the feedback response based at least in part on the change in the activity the user 102-*a* is engaged in. As a result, any of the components of the system 100, including the wearable device 104-*a*, the user device 106-*a* associated with the user 102-*a*, the one or more servers 110, or any combination thereof, may cause the user device 106-*a* to output the adjusted feedback response indicative of the change in the one or more physiological data is based at least in part on the change in the activity the user 102-*a* is engaged in.

In some implementations, any of the components of the system 100, including the wearable device 104-*a*, the user device 106-*a* associated with the user 102-*a*, the one or more servers 110, or any combination thereof, may cause an audio interface of the user device 106-*a* to output the audio pulses. Alternatively, any of the components of the system 100, including the wearable device 104-*a*, the user device 106-*a* associated with the user 102-*a*, the one or more servers 110, or any combination thereof, may cause a GUI of the user device 106-*a* to output the tactile vibration pulses.

In some implementations, any of the components of the system 100, including the wearable device 104-*a*, the user device 106-*a* associated with the user 102-*a*, the one or more servers 110, or any combination thereof, may pair the user device 106-*a* with a Bluetooth device (e.g., a Bluetooth headphones/headset or other Bluetooth speakers) or another wirelessly connected device (e.g. Wi-Fi enabled device or other wireless protocol enabled devices). Any of the components of the system 100, including the wearable device 104-*a*, the user device 106-*a* associated with the user 102-*a*, the one or more servers 110, or any combination thereof, may cause the Bluetooth device to output the audio pulses indicative of the physiological data based at least in part on the pairing. Additionally or alternatively, any of the components of the system 100, including the wearable device 104-*a*, the user device 106-*a* associated with the user 102-*a*, the one or more servers 110, or any combination thereof, may cause the Bluetooth device to output the tactile vibration pulses indicative of the physiological data based at least in part on the pairing. The system 100 may thereby provide real-time biofeedback (e.g., a heart rate and cadence) in the form of the audio pulses, the tactile vibration pulses, or the visible light pulses by connecting any of the components of the system 100, including the wearable device 104-*a*, the user device 106-*a* associated with the user 102-*a*, the one or more servers 110, or any combination thereof with the Bluetooth device.

In some implementations, any of the components of the system 100, including the wearable device 104-*a*, the user device 106-*a* associated with the user 102-*a*, the one or more servers 110, or any combination thereof, may transmit a command to the wearable device 104-*a* to cause an interface (e.g., one or more sensors) of the wearable device 104-*a* to output the tactile vibration pulses or the visible light pulses indicative of the physiological data. For example, the ring 104-*a* may output the tactile vibration pulses or the visible light pulses indicative of the physiological data to the user 102-*a*.

In some implementations, any of the components of the system 100, including the wearable device 104-*a*, the user device 106-*a* associated with the user 102-*a*, the one or more servers 110, or any combination thereof, may synchronize data between two or more users 102. For example, any of the components of the system 100, including the wearable device 104-*a*, the user device 106-*a* associated with the user 102-*a*, the one or more servers 110, or any combination thereof, may receive second physiological data associated with a second user 102-*b*. The second physiological data may include second heart rate data associated with the second user 102-*b*. Any of the components of the system 100, including the wearable device 104-*a*, the user device 106-*a* associated with the user 102-*a*, the one or more servers 110, or any combination thereof, may sync the physiological data associated with the user 102-*a* and the second physiological data associated with the second user 102-*b*. In some implementations, any of the components of the system 100, including the wearable device 104-*a*, the user device 106-*a* associated with the user 102-*a*, the one or more servers 110, or any combination thereof, may sync physiological data across a group of users 102. To sync physiological data, any of the components of the system 100, including the wearable device 104-*a*, the user device 106-*a* associated with the user 102-*a*, the one or more servers 110, or any combination thereof may determine a target heart rate for a group of users 102. A group of users 102 may include two or more users 102. Based at least in part on acquired physiological data from the group of users 102, each user 102 would be guided with individual (or common) feedback for meeting the target heart rate. For example, if a level of one user 102 would be very far away from the selected target heart rate, then they might not benefit from having a similar feedback than the other users 102 that are closer to reaching the target heart rate, but a more granular feedback would be preferred.

In some implementations, any of the components of the system 100, including the wearable device 104-*a*, the user device 106-*a* associated with the user 102-*a*, the one or more servers 110, or any combination thereof, may select audio content from a plurality of audio content based at least in part on the physiological data associated with the user 102-*a*, and output via the user device 106-*a* the audio content to the user 102-*a*.

In some implementations, any of the components of the system 100, including the wearable device 104-*a*, the user device 106-*a* associated with the user 102-*a*, the one or more servers 110, or any combination thereof, may determine a heart rate zone based at least in part on the acquired physiological data associated with the user 102-*a* from the wearable device 104-*a*. In some implementations, any of the components of the system 100, including the wearable device 104-*a*, the user device 106-*a* associated with the user 102-*a*, the one or more servers 110, or any combination thereof, may select the feedback response indicative of the physiological data associated with the user 102-*a* based at least in part on the heart rate zone. The feedback response may be indicative to the user 102-*a* to maintain a heart rate associated with the user 102-*a* within the heart rate zone, or adjust the heart rate associated with the user 102-*a* to switch to a different heart rate zone of a set of heart rate zones associated with the user 102-*a*. The set of heart rate zones may include one or more of a first range of heart rates associated with a first percentage of a maximum heart rate associated with the user 102-*a*, a second range of heart rates associated with a second percentage of the maximum heart rate associated with the user 102-*a*, or a third range of heart rates associated with a third percentage of the maximum heart rate associated with the user 102-*a*, or a combination thereof.

Any of the components of the system 100, including the wearable device 104-*a*, the user device 106-*a* associated with the user 102-*a*, the one or more servers 110, or any combination thereof, may select the feedback response indicative of the physiological data associated with the user 102-*a* based at least in part on a machine learning model. The machine learning model is trained to identify relationships between a respective heart rate data and one or more of a respective magnitude of respective tactile vibration pulses, a respective volume of respective audio pulses, a respective duration of each tactile vibration pulse of the respective tactile vibration pulses, a respective duration of each audio pulse of the respective audio pulses, a respective frequency of the respective tactile vibration pulses, a respective frequency of the respective audio pulses, a respective duration of each visible light pulse of the visible light pulses, a respective brightness of the visible light pulses, or a combination thereof.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
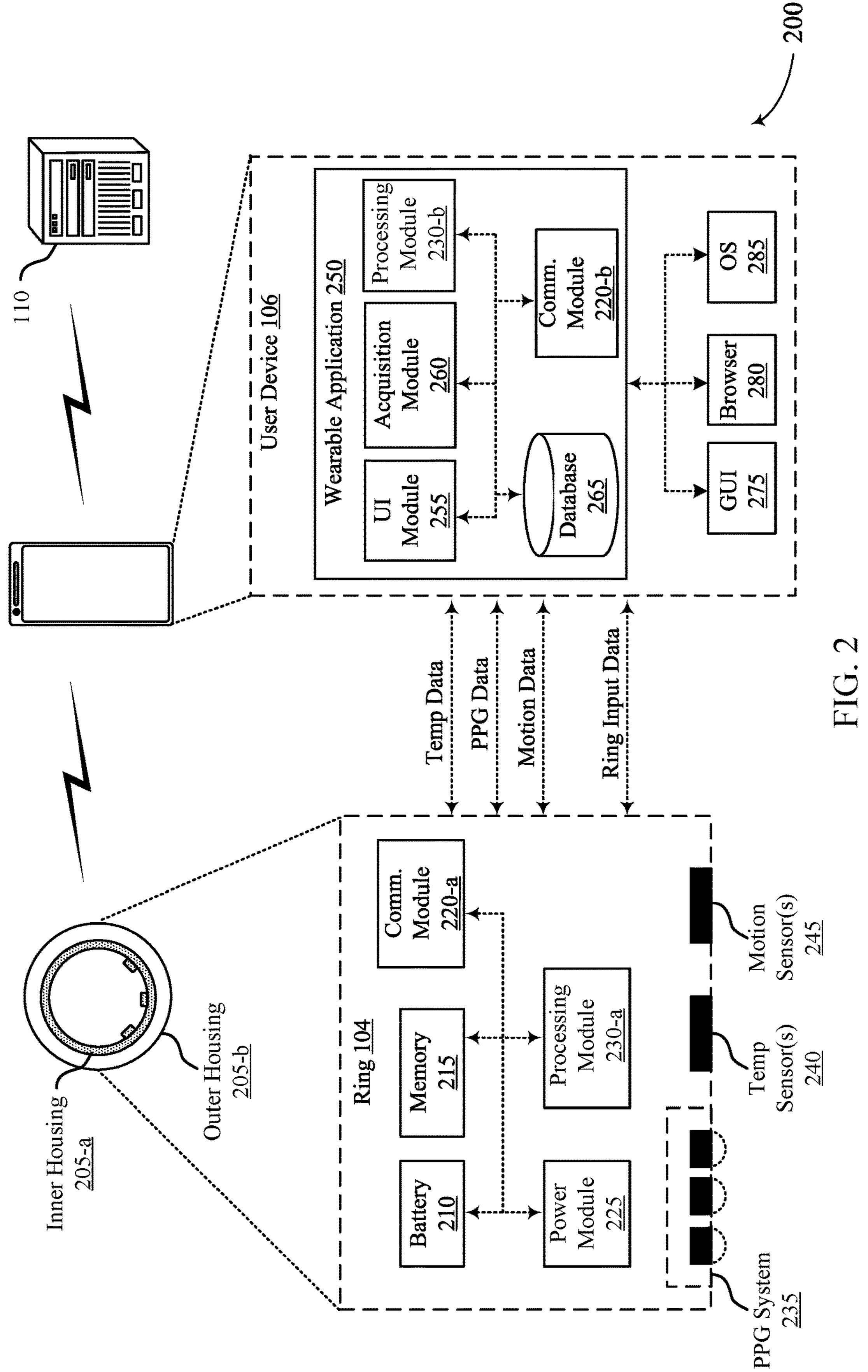
FIG. 2 illustrates an example of a system that supports techniques for biofeedback using heart rate data in accordance with aspects of the present disclosure.

FIG. 2 illustrates an example of a system 200 that supports techniques for biofeedback using heart rate data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate (s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for biofeedback. In particular, the system 200 illustrated in FIG. 2 may support techniques for providing insights to a user 102 by causing a user device 106 corresponding to the user 102 to display insights relevant to the user 102 according to physiological data associated with the user 102. For example, as shown in FIG. 2, a user may be associated with the ring 104 and a user device 106. In this example, the ring 104 may collect physiological data associated with the user, including heart rate. The user device 106 may acquire physiological data associated with the user 102-*a* from the ring 104. The physiological data may include at least heart rate data associated with the user. The user device 106-*a* may select a feedback response indicative of the physiological data associated with the user. The feedback response may include one or more of audio pulses, tactile vibration pulses, or visible light pulses.

The system 200 may provide insights to the user associated with the physiological data of the user using one or more of audio pulses, tactile vibration pulses, or visible light pulses. Put another way, the system 200 may output to the user a representation of a heart rate of the user in the form of audio pulses, tactile vibration pulses, or visible light pulses. Any of the components of the system 200, including the ring 104, the user device 106, the server 110, or any combination thereof, may output a heart rate of the user in the form of audio pulses, tactile vibration pulses, or visible light pulses. In some implementations, the user device 106 may output via the wearable application 250 a representation of a heart rate of the user in the form of audio pulses, tactile vibration pulses, or visible light pulses. In some implementations, the user device 106 may via the GUI 275 output a heart rate of the user in the form of audio pulses, tactile vibration pulses, or visible light pulses as described herein.

Figure 3:
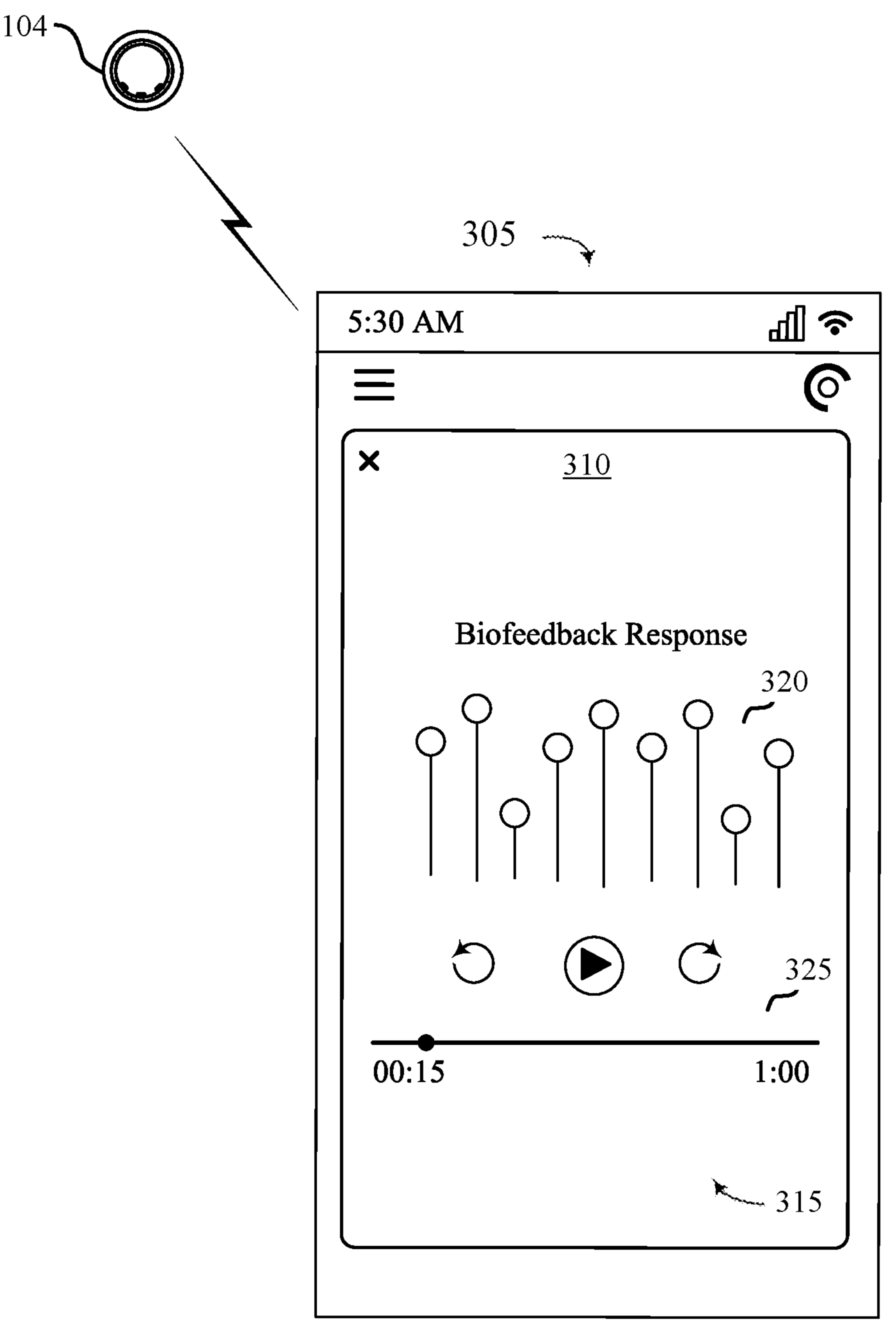
FIGS. 3 through 5 illustrates examples of graphical user interfaces (GUIs) that support techniques for biofeedback using heart rate data in accordance with aspects of the present disclosure.

FIG. 3 illustrates an example of a GUI 300 that supports techniques for biofeedback using heart rate data in accordance with aspects of the present disclosure. The GUI 300 may implement, or be implemented by, aspects of the system 100 or the system 200, or any combination thereof. In some examples, the GUI 300 may be an example of a GUI of a user device 106 that may be examples of GUIs and user devices 106 as described with reference to FIGS. 1 and 2. For example, the GUI 300 may be an example of a GUI 275 of a user device 106 as described with reference to FIG. 2. In the example of FIG. 3, the GUI 300 may include an application interface 305 that may be displayed to a user via the GUI 300.

The application interface 305 may be associated with an application running on a user device 106. In some examples, the application interface 305 may include a set of graphical elements the application provides so that a user 102 may provide input to, and receive output from, the application via the application interface 305. For example, the application interface 305 may include a graphical element 310 that may output a biofeedback response 315 (e.g., one or more audio pulses 320, audio content 325 (e.g., a song)) to a user 102 corresponding to a user device 106 associated with the GUI 300. As described herein, the biofeedback response 315 may be selected, determined, and/or output by any of the components of the system 100 and/or the system 200, including a ring 104, a user device 106 associated with a user 102, one or more servers 110, or any combination thereof, and may be based at least in part on acquired physiological data associated with the user 102 by the ring 104.

For example, any of the components of the system 100 and/or the system 200, including a ring 104, a user device 106 associated with a user 102, one or more servers 110, or any combination thereof may determine and/or select the biofeedback response 315 based at least in part on an activity the user 102 is engaged in. Additionally or alternatively, any of the components of the system 100 and/or the system 200, including a ring 104, a user device 106 associated with a user 102, one or more servers 110, or any combination thereof may determine and/or select the biofeedback response 315 based at least in part on a Readiness Score or a Sleep Score associated with the user 102, or any other score or data (e.g., a breathing rate associated with the user 102, daytime heart rate associated with the user 102, a stress level associated with the user 102).

The biofeedback response 315 may be output via an audio interface of the user device 106. For example, the audio interface may include one or more speakers of the user device 106 that may output the biofeedback response 315 in the form of one or more audio pulses 320 or other audio content 325 (e.g., a song with a base rhythm that matches or is similar to the heart rate of the user 102). Any of the components of the system 100 and/or the system 200, including a ring 104, a user device 106 associated with a user 102, one or more servers 110, or any combination thereof may determine a volume of the one or more audio pulses 320 and/or audio content 325, for example, based at least in part on the heart rate of the user 102. Any of the components of the system 100 and/or the system 200, including a ring 104, a user device 106 associated with a user 102, one or more servers 110, or any combination thereof may determine a duration of each audio pulse of the audio pulses 320 and/or a duration of the audio content 325, for example, based at least in part on the heart rate of the user 102. Any of the components of the system 100 and/or the system 200, including a ring 104, a user device 106 associated with a user 102, one or more servers 110, or any combination thereof may determine a frequency of the audio pulses 320, for example, based at least in part on the heart rate of the user 102.

The biofeedback response 315 may be indicative to the user 102 for regulating (e.g., maintaining, adjusting, switching, increasing, decreasing, and the like) a heart rate of the user 102. In some examples, the biofeedback response 315 may indicate to the user 102, to maintain a heart rate of the user 102 at a current level (e.g., a current beats per minute), using one or more audio pulses 320 and/or audio content 325, and based at least in part on an activity the user 102 is engaged in. For example, if the user 102 wants to maintain a heart rate at a current heart rate, then the biofeedback response 315 may correspond to the current heart rate. Alternatively, the biofeedback response 315 may indicate to the user 102, to adjust (e.g., increase or decrease) a heart rate of the user 102 from a current level, using one or more audio pulses 320 and/or audio content 325, and based at least in part on an activity the user 102 is engaged in. For example, if the user 102 wants to increase their heart rate, such as before an activity (e.g., physical exercise, and the like), or decrease their heart rate after the activity or to reduce the uses 102 stress level, then the biofeedback response 315 may output a higher or lower heart rate in the form of one or more of audio pulses 320. In some examples, the biofeedback response 315 may be output to the user 102 until a target heart rate is met.

In some other implementations, any of the components of the system 100 and/or the system 200, including a ring 104, a user device 106 associated with a user 102, one or more servers 110, or any combination thereof may determine a heart rate zone associated with the user 102 and select the biofeedback response 315 in the form of one or more of audio pulses 320 and/or audio content 325 (e.g., song) to regulate (e.g., maintain, increase, decrease, and the like) the heart rate of the user 102 within the heart rate zone associated with the user 102 or to switch to a different heart rate zone of a set of heart rate zones associated with the user 102.

Although described with reference to the user device 106, in some implementations, a wearable device 104 (e.g., a ring 104) may output the biofeedback response 315 (e.g., one or more audio pulses 320 or other audio content 325) to a user 102.

Figure 4:
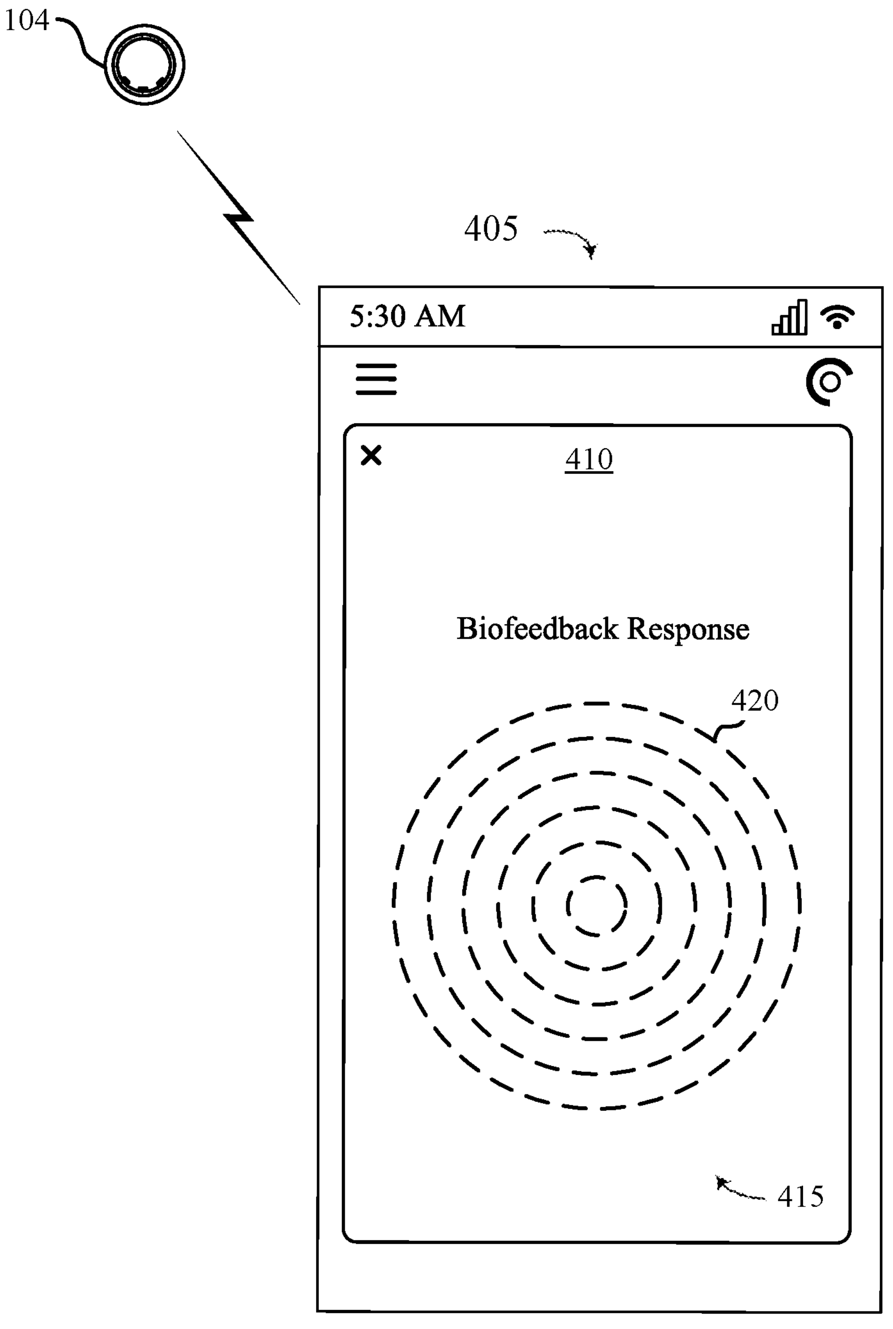

FIG. 4 illustrates an example of a GUI 400 that supports techniques for biofeedback using heart rate data in accordance with aspects of the present disclosure. The GUI 400 may implement, or be implemented by, aspects of the system 100 or the system 200, or any combination thereof. In some examples, the GUI 400 may be an example of a GUI of a user device 106 that may be examples of GUIs and user devices 106 as described with reference to FIGS. 1 and 2. For example, the GUI 400 may be an example of a GUI 275 of a user device 106 as described with reference to FIG. 2. In the example of FIG. 4, the GUI 400 may include an application interface 405 that may be displayed to a user via the GUI 400.

The application interface 405 may be associated with an application running on a user device 106. In some examples, the application interface 405 may include a set of graphical elements the application provides so that a user 102 may provide input to, and receive output from, the application via the application interface 405. For example, the application interface 405 may include a graphical element 410 that may output a biofeedback response 415 (e.g., one or more tactile vibration pulses 420) to a user 102 corresponding to a user device 106 associated with the GUI 400. As described herein, the biofeedback response 415 may be selected, determined, and/or output by any of the components of the system 100 and/or the system 200, including a ring 104, a user device 106 associated with a user 102, one or more servers 110, or any combination thereof, and may be based at least in part on acquired physiological data associated with the user 102 by the ring 104.

For example, any of the components of the system 100 and/or the system 200, including a ring 104, a user device 106 associated with a user 102, one or more servers 110, or any combination thereof may determine and/or select the biofeedback response 415 based at least in part on an activity the user 102 is engaged in. Additionally or alternatively, any of the components of the system 100 and/or the system 200, including a ring 104, a user device 106 associated with a user 102, one or more servers 110, or any combination thereof may determine and/or select the biofeedback response 415 based at least in part on a Readiness Score or a Sleep Score associated with the user 102, or any other score or data (e.g., a breathing rate associated with the user 102, daytime heart rate associated with the user 102, a stress level associated with the user 102).

The biofeedback response 415 may be output via the GUI 400 of the user device 106. For example, the GUI 400 may include one or more tactile vibration sensors that may output the biofeedback response 415 in the form of one or more tactile vibration pulses 420 that match or are similar to the heart rate of the user 102. Any of the components of the system 100 and/or the system 200, including a ring 104, a user device 106 associated with a user 102, one or more servers 110, or any combination thereof may determine a magnitude of the tactile vibration pulses 420, for example, based at least in part on the heart rate of the user 102. Any of the components of the system 100 and/or the system 200, including a ring 104, a user device 106 associated with a user 102, one or more servers 110, or any combination thereof may determine a duration of each tactile vibration pulse of the tactile vibration pulses 420, for example, based at least in part on the heart rate of the user 102. Any of the components of the system 100 and/or the system 200, including a ring 104, a user device 106 associated with a user 102, one or more servers 110, or any combination thereof may determine a frequency of the tactile vibration pulses 420, for example, based at least in part on the heart rate of the user 102.

The biofeedback response 415 may be indicative to the user 102 for regulating (e.g., maintaining, adjusting, switching, increasing, decreasing, and the like) a heart rate of the user 102. For example, the biofeedback response 415 may indicate to the user 102, to maintain a heart rate of the user 102 at a current level (e.g., a current beats per minute), using the one or more tactile vibration pulses 420 and based at least in part on an activity the user 102 is engaged in. Alternatively, the biofeedback response 415 may indicate to the user 102, to adjust (e.g., increase or decrease) a heart rate of the user 102 from a current level, using the one or more tactile vibration pulses 420 and based at least in part on an activity the user 102 is engaged in.

In some other implementations, any of the components of the system 100 and/or the system 200, including a ring 104, a user device 106 associated with a user 102, one or more servers 110, or any combination thereof may determine a heart rate zone associated with the user 102 and select the biofeedback response 415 in the form of one or more tactile vibration pulses 420 to regulate (e.g., maintain, increase, decrease, and the like) the heart rate of the user 102 within the heart rate zone associated with the user 102 or to switch to a different heart rate zone of a set of heart rate zones associated with the user 102.

The user 102 may participate in an endurance training that may require the user 102 to exercises in one or more heart rate zones. For example, in endurance training, the user 102 may perform certain exercises in a certain heart rate zone. The one or more heart rate zones may include a first endurance zone, a second endurance zone, and a third endurance zone (e.g., a maximum heart rate zone). In some cases, during the endurance training it might be difficult for the user 102 to know whether they are maintaining a target heart rate zone, whether they are in an appropriate heart rate zone, and/or whether they are transitioning from one heart rate zone to another heart rate zone.

In some implementations, the user 102 may use an LED, for example, an external Bluetooth LED device (e.g., the user device 106) attached to the user 102 field of vision or a wearable device 104 (e.g., a ring 104) that may be visible to the user 102 from the ring opening) to indicate to the user 102 whether they are maintaining a target heart rate zone, whether they are in an appropriate heart rate zone, and/or whether they are transitioning from one heart rate zone to another heart rate zone, or any combination thereof. In some other implementations, the user 102 may be notified whether they are maintaining a target heart rate zone, whether they are in an appropriate heart rate zone, and/or whether they are transitioning from one heart rate zone to another heart rate zone, or any combination thereof, based on a sound or vibration output via an application running on the user device 106 or via the wearable device 104.

In other implementations, with reference to FIG. 4, the user 102 may hold a finger over the GUI 400 that may display one or more parts of heart rate graph associated with the user 102, and the user 102 may sense (e.g., feel) through the GUI 400 a beating heart in the rate that it was measured at that time. Additionally or alternatively, the user 102 may sense (e.g., feel) through the GUI 400 their current heart rate. In some other examples, the user 102 may sense (e.g., feel) through the GUI 400 an adjusted heart rate (e.g., slower or faster heart rate) that is output to the user 102, for example, based on the user's activity or selected target heart rate that user might want to meet.

Although described with reference to the user device 106, in some implementations, a wearable device 104 (e.g., a ring 104) may output the biofeedback response 415 (e.g., one or more tactile vibration pulses 420) to a user 102.

Figure 5:
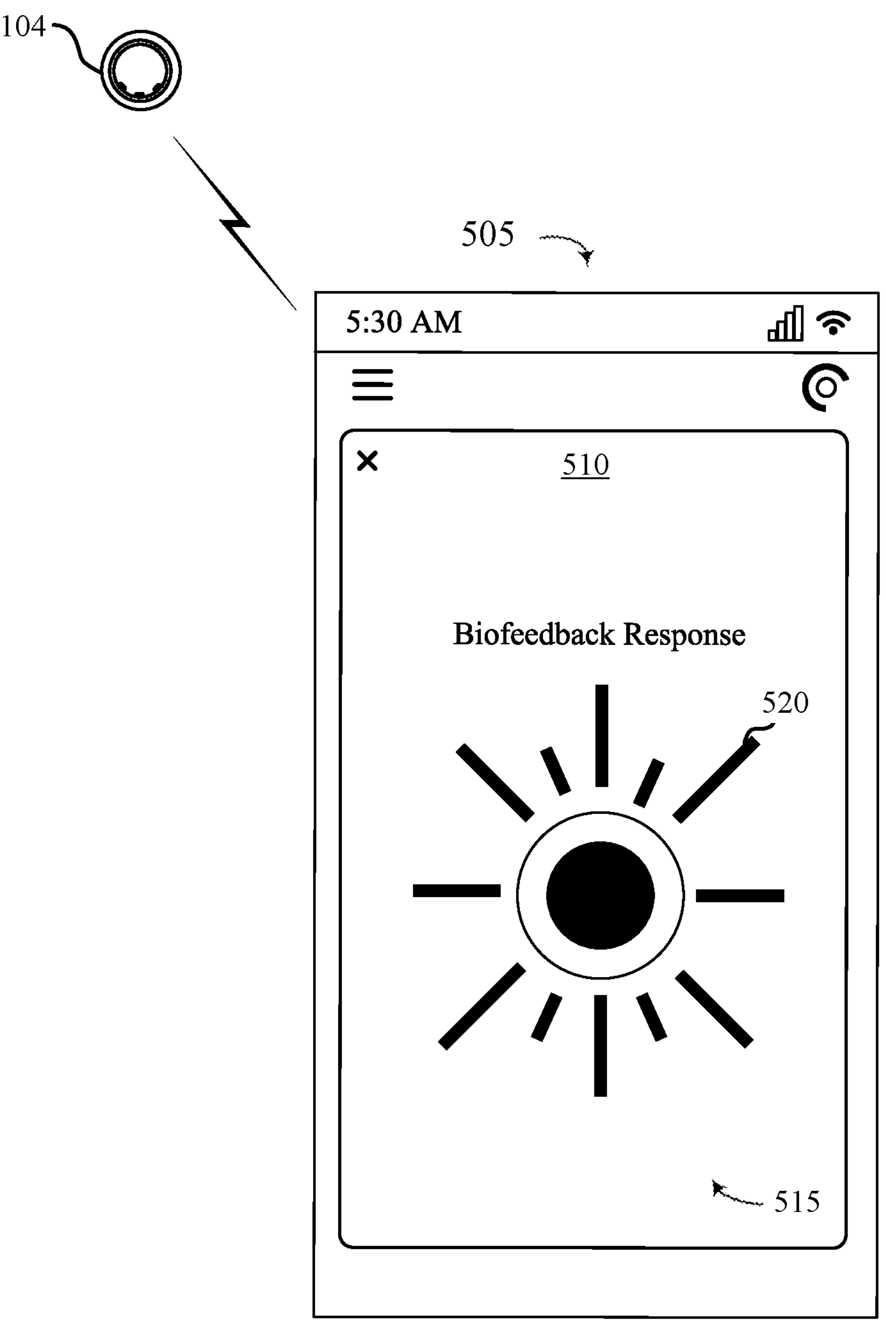

FIG. 5 illustrates an example of a GUI 500 that supports techniques for biofeedback using heart rate data in accordance with aspects of the present disclosure. The GUI 500 may implement, or be implemented by, aspects of the system 100 or the system 200, or any combination thereof. In some examples, the GUI 500 may be an example of a GUI of a user device 106 that may be examples of GUIs and user devices 106 as described with reference to FIGS. 1 and 2. For example, the GUI 500 may be an example of a GUI 275 of a user device 106 as described with reference to FIG. 2. In the example of FIG. 5, the GUI 500 may include an application interface 505 that may be displayed to a user via the GUI 500.

The application interface 505 may be associated with an application running on a user device 106. In some examples, the application interface 505 may include a set of graphical elements the application provides so that a user 102 may provide input to, and receive output from, the application via the application interface 505. For example, the application interface 505 may include a graphical element 510 that may output a biofeedback response 515 (e.g., one or more visible light pulses 520) to a user 102 corresponding to a user device 106 associated with the GUI 500. As described herein, the biofeedback response 515 may be selected, determined, and/or output by any of the components of the system 100 and/or the system 200, including a ring 104, a user device 106 associated with a user 102, one or more servers 110, or any combination thereof, and may be based at least in part on acquired physiological data associated with the user 102 by the ring 104.

For example, any of the components of the system 100 and/or the system 200, including a ring 104, a user device 106 associated with a user 102, one or more servers 110, or any combination thereof may determine and/or select the biofeedback response 515 based at least in part on an activity the user 102 is engaged in. Additionally or alternatively, any of the components of the system 100 and/or the system 200, including a ring 104, a user device 106 associated with a user 102, one or more servers 110, or any combination thereof may determine and/or select the biofeedback response 515 based at least in part on a Readiness Score or a Sleep Score associated with the user 102, or any other score or data (e.g., a breathing rate associated with the user 102, daytime heart rate associated with the user 102, a stress level associated with the user 102).

The biofeedback response 515 may be output via the GUI 500 of the user device 106. For example, the GUI 500 may include one or more visible light sensors that may output the biofeedback response 515 in the form of one or more visible light pulses 520 that match or are similar to the heart rate of the user 102. Any of the components of the system 100 and/or the system 200, including a ring 104, a user device 106 associated with a user 102, one or more servers 110, or any combination thereof may determine a duration of each visible light pulse of the visible light pulses 520, for example, based at least in part on the heart rate of the user 102. Any of the components of the system 100 and/or the system 200, including a ring 104, a user device 106 associated with a user 102, one or more servers 110, or any combination thereof may determine a brightness of the visible light pulses 520, for example, based at least in part on the heart rate of the user 102.

The biofeedback response 515 may be indicative to the user 102 for regulating (e.g., maintaining, adjusting, switching, increasing, decreasing, and the like) a heart rate of the user 102. For example, the biofeedback response 515 may indicate to the user 102, to maintain a heart rate of the user 102 at a current level (e.g., a current beats per minute), using the one or more visible light pulses 520 and based at least in part on an activity the user 102 is engaged in. Alternatively, the biofeedback response 515 may indicate to the user 102, to adjust (e.g., increase or decrease) a heart rate of the user 102 from a current level, using the one or more visible light pulses 520 and based at least in part on an activity the user 102 is engaged in.

In some other implementations, any of the components of the system 100 and/or the system 200, including a ring 104, a user device 106 associated with a user 102, one or more servers 110, or any combination thereof may determine a heart rate zone associated with the user 102 and select the biofeedback response 515 in the form of one or more visible light pulses 520 to regulate (e.g., maintain, increase, decrease, and the like) the heart rate of the user 102 within the heart rate zone associated with the user 102 or to switch to a different heart rate zone of a set of heart rate zones associated with the user 102.

Although described with reference to the user device 106, in some implementations, a wearable device 104 (e.g., a ring 104) may output the biofeedback response 515 (e.g., one or more visible light pulses 520) to a user 102.

Figure 6:
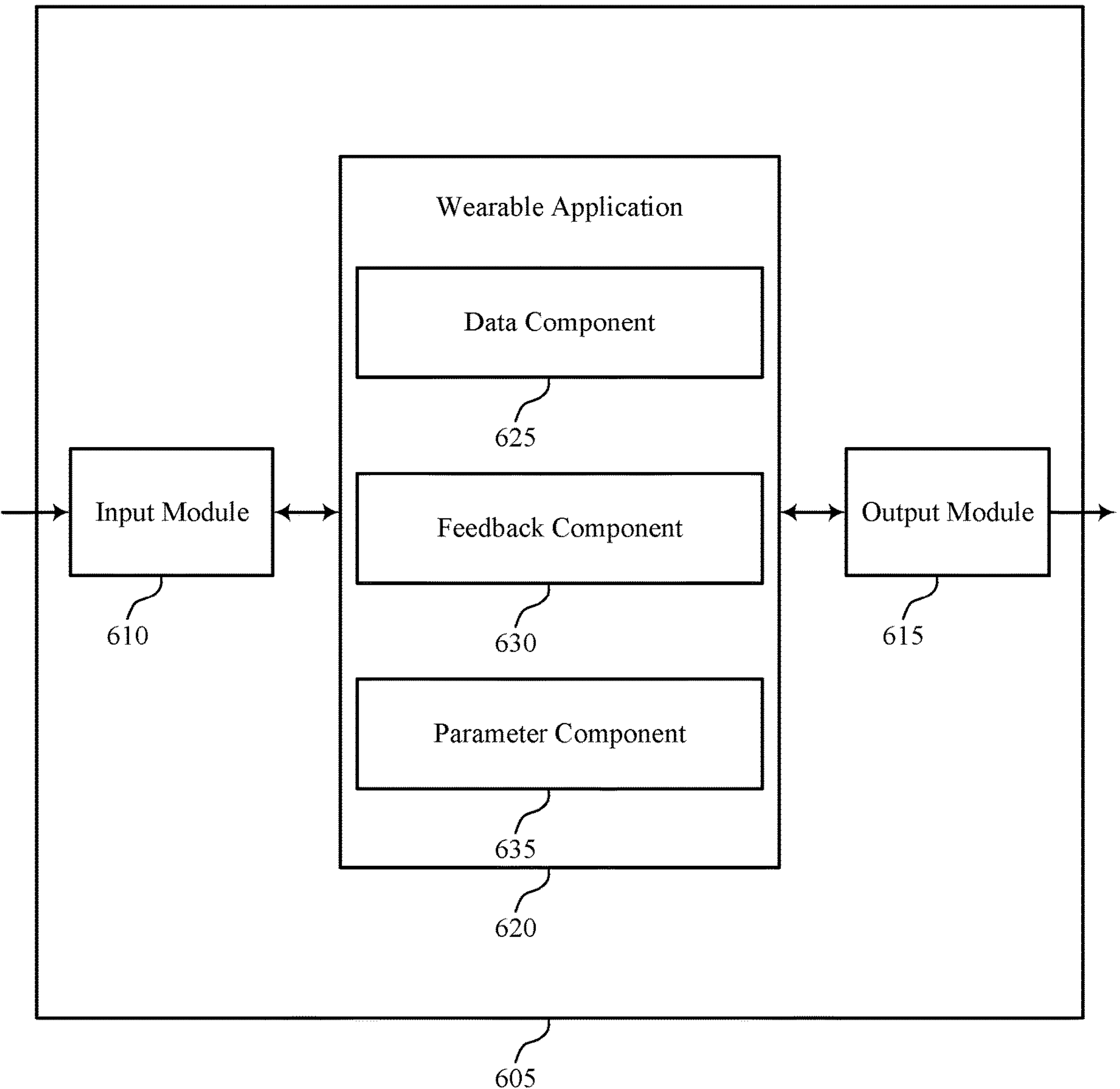
FIG. 6 illustrates a block diagram of an apparatus that supports techniques for biofeedback using heart rate data in accordance with aspects of the present disclosure.

FIG. 6 illustrates a block diagram 600 of a device 605 that supports techniques for biofeedback using heart rate data in accordance with aspects of the present disclosure. The device 605 may include an input module 610, an output module 615, and a wearable application 620. The device 605 may also include a processor. Each of these components may be in communication with one another (e.g., via one or more buses).

The input module 610 may provide a means for receiving information such as packets, user data, control information, or any combination thereof associated with various information channels (e.g., control channels, data channels, information channels related to illness detection techniques). Information may be passed on to other components of the device 605. The input module 610 may utilize a single antenna or a set of multiple antennas.

The output module 615 may provide a means for transmitting signals generated by other components of the device 605. For example, the output module 615 may transmit information such as packets, user data, control information, or any combination thereof associated with various information channels (e.g., control channels, data channels, information channels related to illness detection techniques). In some examples, the output module 615 may be co-located with the input module 610 in a transceiver module. The output module 615 may utilize a single antenna or a set of multiple antennas.

For example, the wearable application 620 may include a data component 625, a feedback component 630, a parameter component 635, or any combination thereof. In some examples, the wearable application 620, or various components thereof, may be configured to perform various operations (e.g., receiving, monitoring, transmitting) using or otherwise in cooperation with the input module 610, the output module 615, or both. For example, the wearable application 620 may receive information from the input module 610, send information to the output module 615, or be integrated in combination with the input module 610, the output module 615, or both to receive information, transmit information, or perform various other operations as described herein.

The wearable application 620 may support biofeedback in accordance with examples as disclosed herein. The data component 625 may be configured as or otherwise support a means for acquiring physiological data associated with a user from a wearable device, the physiological data comprising at least heart rate data associated with the user. The feedback component 630 may be configured as or otherwise support a means for selecting a feedback response indicative of the physiological data associated with the user, the feedback response comprising one or more of audio (e.g., audio pulses), haptic (e.g., tactile vibration pulses), or visible light feedback (e.g., visible light pulses). The parameter component 635 may be configured as or otherwise support a means for determining one or more parameters for the feedback response based at least in part on the physiological data. The one or more parameters comprising one or more of a magnitude, a duration, or a frequency, associated with one or more of the audio, haptic, or visible light feedback. For example, the one or more parameters may comprise a magnitude of the haptic feedback (e.g., tactile vibration pulses), a volume of the audio feedback (e.g., audio pulses), a duration of each haptic feedback (e.g., tactile vibration pulse), a duration of each audio feedback (e.g., audio pulse), a frequency of the haptic feedback (e.g., tactile vibration pulses), a frequency of the audio feedback (e.g., audio pulses), a duration of each visible light feedback (e.g., visible light pulse), a brightness of the visible light feedback (e.g. the visible light pulses), or a combination thereof. The feedback component 630 may be configured as or otherwise support a means for causing a user device (e.g., the device 605) or the wearable device to output the feedback response indicative of the physiological data in accordance with the one or more parameters for the feedback response, the feedback response indicative to the user for regulating one or more of the physiological data associated with the user.

Figure 7:
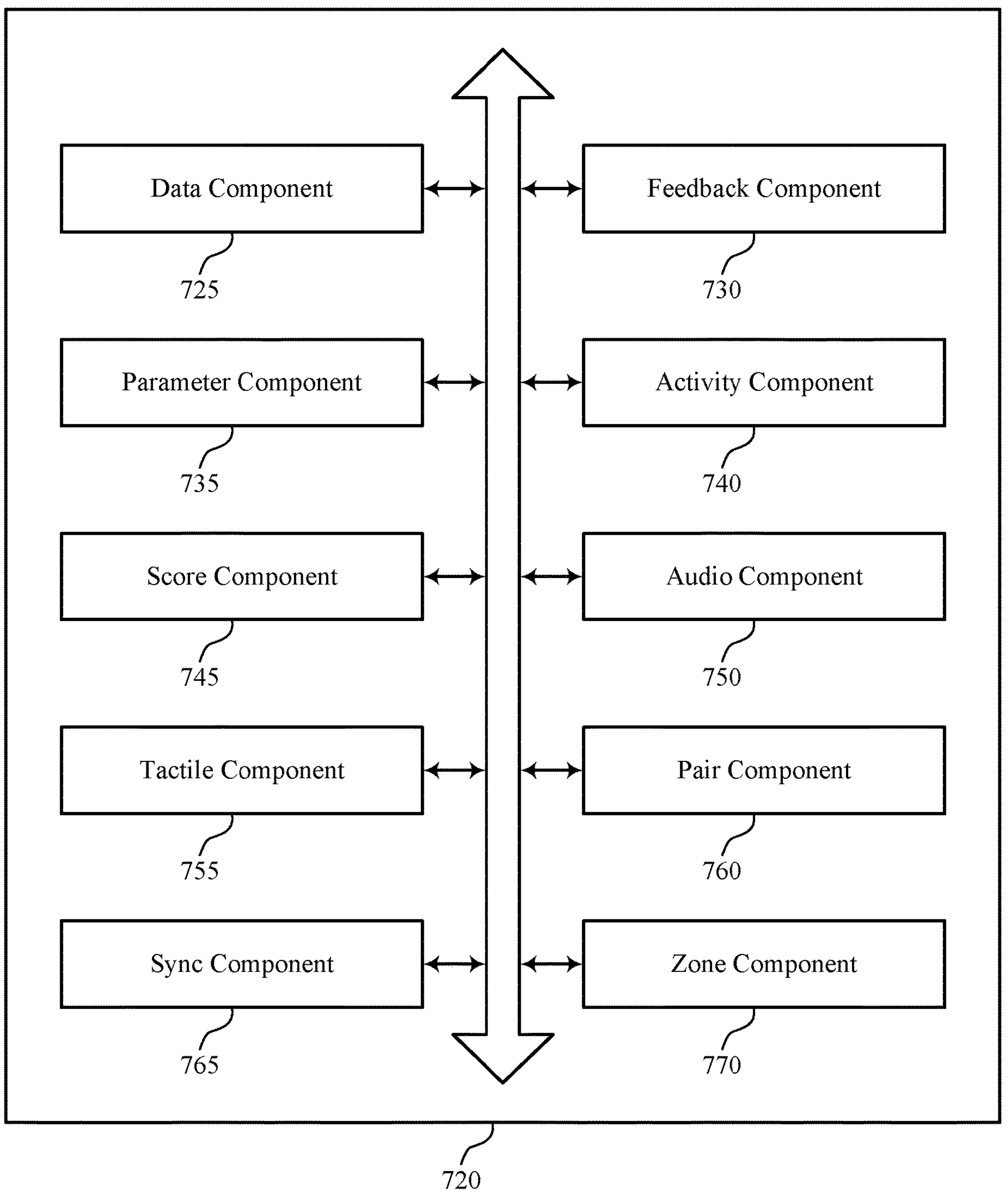
FIG. 7 illustrates a block diagram of a wearable application that supports techniques for biofeedback using heart rate data in accordance with aspects of the present disclosure.

FIG. 7 illustrates a block diagram 700 of a wearable application 720 that supports techniques for biofeedback using heart rate data in accordance with aspects of the present disclosure. The wearable application 720 may be an example of aspects of a wearable application or a wearable application 620, or both, as described herein. The wearable application 720, or various components thereof, may be an example of means for performing various aspects of techniques for biofeedback using heart rate data as described herein. For example, the wearable application 720 may include a data component 725, a feedback component 730, a parameter component 735, an activity component 740, a score component 745, an audio component 750, a tactile component 755, a pair component 760, a sync component 765, a zone component 770, or any combination thereof. Each of these components may communicate, directly or indirectly, with one another (e.g., via one or more buses).

The wearable application 720 may support biofeedback in accordance with examples as disclosed herein. The data component 725 may be configured as or otherwise support a means for acquiring physiological data associated with a user from a wearable device, the physiological data comprising at least heart rate data associated with the user. The feedback component 730 may be configured as or otherwise support a means for selecting a feedback response indicative of the physiological data associated with the user, the feedback response comprising one or more of audio (e.g., audio pulses), haptic (e.g., tactile vibration pulses), or visible light feedback (e.g., visible light pulses). The parameter component 735 may be configured as or otherwise support a means for determining one or more parameters for the feedback response based at least in part on the physiological data. The one or more parameters comprising a magnitude, a duration, or a frequency, associated with one or more of the audio, haptic, or visible light feedback. In some examples, the feedback component 730 may be configured as or otherwise support a means for causing a user device or the wearable device to output the feedback response indicative of the physiological data in accordance with the one or more parameters for the feedback response, the feedback response indicative to the user for regulating one or more of the physiological data associated with the user.

In some examples, the activity component 740 may be configured as or otherwise support a means for determining an activity the user is engaged in based at least in part on sensor data from the wearable device. In some examples, the feedback component 730 may be configured as or otherwise support a means for selecting the feedback response, determining the one or more parameters for the feedback response, or both, based at least in part on the activity the user is engaged in.

In some examples, the score component 745 may be configured as or otherwise support a means for identifying a Readiness Score or a Sleep Score associated with the user. In some examples, the feedback component 730 may be configured as or otherwise support a means selecting the feedback response, determining the one or more parameters for the feedback response, or both, based at least in part on the Readiness Score or the Sleep Score associated with the user.

In some examples, the data component 725 may be configured as or otherwise support a means for determining a change in one or more physiological data associated with the user after outputting the feedback response indicative of the physiological data to the user. In some examples, the feedback component 730 may be configured as or otherwise support a means for adjusting the feedback response including the one or more parameters for the feedback response based at least in part on the change in the one or more physiological data associated with the user. In some examples, the feedback component 730 may be configured as or otherwise support a means for causing the user device or the wearable device to output the adjusted feedback response indicative of the change in the one or more physiological data in accordance with the one or more adjusted parameters for the feedback response.

In some examples, the activity component 740 may be configured as or otherwise support a means for determining a change in an activity the user is engaged in based at least in part on sensor data from the wearable device. In some examples, the feedback component 730 may be configured as or otherwise support a means for adjusting the feedback response including the one or more parameters for the feedback response based at least in part on the change in the activity the user is engaged in. In some examples, the feedback component 730 may be configured as or otherwise support a means for causing the user device or the wearable device to output the adjusted feedback response indicative of the change in the one or more physiological data based at least in part on the change in the activity the user is engaged in.

In some examples, to support adjusting the one or more parameters for the feedback response, the feedback component 730 may be configured as or otherwise support a means for increasing or decreasing one or more of the magnitude, the duration, or the frequency, associated with one or more of the audio, haptic, or visible light feedback.

In some examples, to support outputting the feedback response indicative of the physiological data, the audio component 750 may be configured as or otherwise support a means for causing an audio interface of the user device to output the audio feedback (e.g., audio pulses, audio content, or the like). In some examples, to support outputting the feedback response indicative of the physiological data, the tactile component 755 may be configured as or otherwise support a means for causing a GUI of the user device to output the haptic feedback (e.g., tactile vibration pulses, or the like).

In some examples, the pair component 760 may be configured as or otherwise support a means for pairing the user device with a Bluetooth device. In some examples, the audio component 750 may be configured as or otherwise support a means for causing the Bluetooth device to output the audio feedback (e.g., audio pulses, audio content, or the like) indicative of the physiological data based at least in part on the pairing. In some examples, the tactile component 755 may be configured as or otherwise support a means for causing the Bluetooth device to output the haptic feedback (e.g., tactile vibration pulses, or the like) indicative of the physiological data based at least in part on the pairing.

In some examples, to support causing the user device or the wearable device to output the feedback response indicative of the physiological data, the feedback component 730 may be configured as or otherwise support a means for transmitting a command to the wearable device to cause an interface of the wearable device to output the haptic feedback (e.g., tactile vibration pulses, or the like) or the visible light feedback (e.g., visible light pulses, or the like) indicative of the physiological data.

In some examples, the data component 725 may be configured as or otherwise support a means for receiving second physiological data associated with a second user, the second physiological data comprising second heart rate data associated with the second user. In some examples, the sync component 765 may be configured as or otherwise support a means for synching the physiological data associated with the user and the second physiological data associated with the second user. The synching comprises selecting a target heart rate based at least in part on the physiological data associated with the user and the second physiological data associated with the second user. In some examples, the parameter component 735 may be configured as or otherwise support a means for determining the one or more parameters for the feedback response based at least in part on the synching.

In some examples, the audio component 750 may be configured as or otherwise support a means for selecting audio content from a plurality of audio content based at least in part on the physiological data associated with the user. In some examples, the audio component 750 may be configured as or otherwise support a means for outputting via the user device the audio content to the user.

In some examples, the zone component 770 may be configured as or otherwise support a means for determining a heart rate zone based at least in part on the acquired physiological data associated with the user from the wearable device. In some examples, the feedback component 730 may be configured as or otherwise support a means for selecting the feedback response indicative of the physiological data associated with the user based at least in part on the heart rate zone.

In some examples, the feedback response is indicative to the user to maintain a heart rate associated with the user within the heart rate zone, or adjust the heart rate associated with the user to switch to a different heart rate zone of a set of heart rate zones associated with the user.

In some examples, the set of heart rate zones comprises one or more of a first range of heart rates associated with a first percentage of a maximum heart rate associated with the user, a second range of heart rates associated with a second percentage of the maximum heart rate associated with the user, or a third range of heart rates associated with a third percentage of the maximum heart rate associated with the user, or a combination thereof.

In some examples, selecting the feedback response indicative of the physiological data associated with the user is based at least in part on a machine learning model. In some examples, the machine learning model is trained to identify relationships between a respective heart rate data and one or more of a respective magnitude, a respective duration, or a respective frequency, associated with one or more of a respective audio, haptic, or visible light feedback.

In some examples, one or more of the audio, the haptic, or the visible light feedback are generated based at least in part on the heart rate data associated with the user, or both.

In some examples, the wearable device comprises a wearable ring device.

Figure 8:
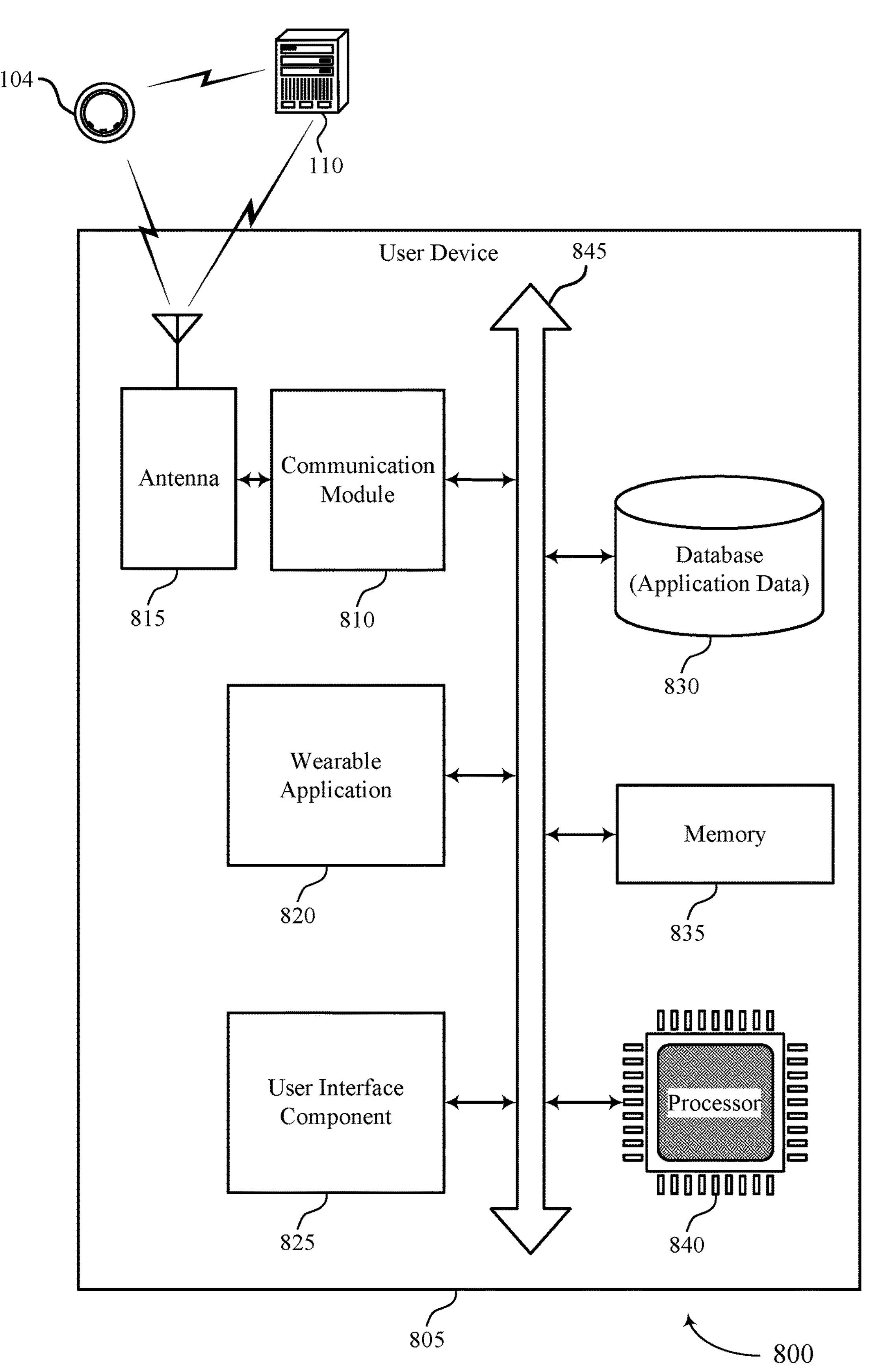
FIG. 8 illustrates a diagram of a system including a device that supports techniques for biofeedback using heart rate data in accordance with aspects of the present disclosure.

FIG. 8 illustrates a diagram of a system 800 including a device 805 that supports techniques for biofeedback using heart rate data in accordance with aspects of the present disclosure. The device 805 may be an example of or include the components of a device 605 as described herein. The device 805 may include an example of a user device 106, as described previously herein. The device 805 may include components for bi-directional communications including components for transmitting and receiving communications with a wearable device 104 and a server 110, such as a wearable application 820, a communication module 810, an antenna 815, a user interface component 825, a database (application data) 830, a memory 835, and a processor 840. These components may be in electronic communication or otherwise coupled (e.g., operatively, communicatively, functionally, electronically, electrically) via one or more buses (e.g., a bus 845).

The communication module 810 may manage input and output signals for the device 805 via the antenna 815. The communication module 810 may include an example of the communication module 220-*b* of the user device 106 shown and described in FIG. 2. In this regard, the communication module 810 may manage communications with the ring 104 and the server 110, as illustrated in FIG. 2. The communication module 810 may also manage peripherals not integrated into the device 805. In some cases, the communication module 810 may represent a physical connection or port to an external peripheral. In some cases, the communication module 810 may utilize an operating system such as iOS®, ANDROID®, MS-DOS®, MS-WINDOWS®, OS/2®, UNIX®, LINUX®, or another known operating system. In other cases, the communication module 810 may represent or interact with a wearable device (e.g., ring 104), modem, a keyboard, a mouse, a touchscreen, or a similar device. In some cases, the communication module 810 may be implemented as part of the processor 840. In some examples, a user may interact with the device 805 via the communication module 810, user interface component 825, or via hardware components controlled by the communication module 810.

In some cases, the device 805 may include a single antenna 815. However, in some other cases, the device 805 may have more than one antenna 815, which may be capable of concurrently transmitting or receiving multiple wireless transmissions. The communication module 810 may communicate bi-directionally, via the one or more antennas 815, wired, or wireless links as described herein. For example, the communication module 810 may represent a wireless transceiver and may communicate bi-directionally with another wireless transceiver. The communication module 810 may also include a modem to modulate the packets, to provide the modulated packets to one or more antennas 815 for transmission, and to demodulate packets received from the one or more antennas 815.

The user interface component 825 may manage data storage and processing in a database 830. In some cases, a user may interact with the user interface component 825. In other cases, the user interface component 825 may operate automatically without user interaction. The database 830 may be an example of a single database, a distributed database, multiple distributed databases, a data store, a data lake, or an emergency backup database.

The memory 835 may include RAM and ROM. The memory 835 may store computer-readable, computer-executable software including instructions that, when executed, cause the processor 840 to perform various functions described herein. In some cases, the memory 835 may contain, among other things, a BIOS which may control basic hardware or software operation such as the interaction with peripheral components or devices.

The processor 840 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 840 may be configured to operate a memory array using a memory controller. In other cases, a memory controller may be integrated into the processor 840. The processor 840 may be configured to execute computer-readable instructions stored in a memory 835 to perform various functions (e.g., functions or tasks supporting a method and system for sleep staging algorithms).

The wearable application 820 may support biofeedback in accordance with examples as disclosed herein. For example, the wearable application 820 may be configured as or otherwise support a means for acquiring physiological data associated with a user from a wearable device, the physiological data comprising at least heart rate data associated with the user. The wearable application 820 may be configured as or otherwise support a means for selecting a feedback response indicative of the physiological data associated with the user, the feedback response comprising one or more of audio, haptic, or visible light feedback. The wearable application 820 may be configured as or otherwise support a means for determining one or more parameters for the feedback response based at least in part on the physiological data. The one or more parameters comprising one or more of a magnitude, a duration, or a frequency, associated with one or more of the audio, haptic, or visible light feedback. The wearable application 820 may be configured as or otherwise support a means for causing a user device (e.g., the device 805) or the wearable device to output the feedback response indicative of the physiological data in accordance with the one or more parameters for the feedback response, the feedback response indicative to the user for regulating one or more of the physiological data associated with the user.

By including or configuring the wearable application 820 in accordance with examples as described herein, the device 805 may support techniques for reduced power consumption.

The wearable application 820 may include an application (e.g., "app"), program, software, or other component which is configured to facilitate communications with a ring 104, server 110, other user devices 106, and the like. For example, the wearable application 820 may include an application executable on a user device 106 which is configured to receive data (e.g., physiological data) from a ring 104, perform processing operations on the received data, transmit and receive data with the servers 110, and cause presentation of data to a user 102.

Figure 9:
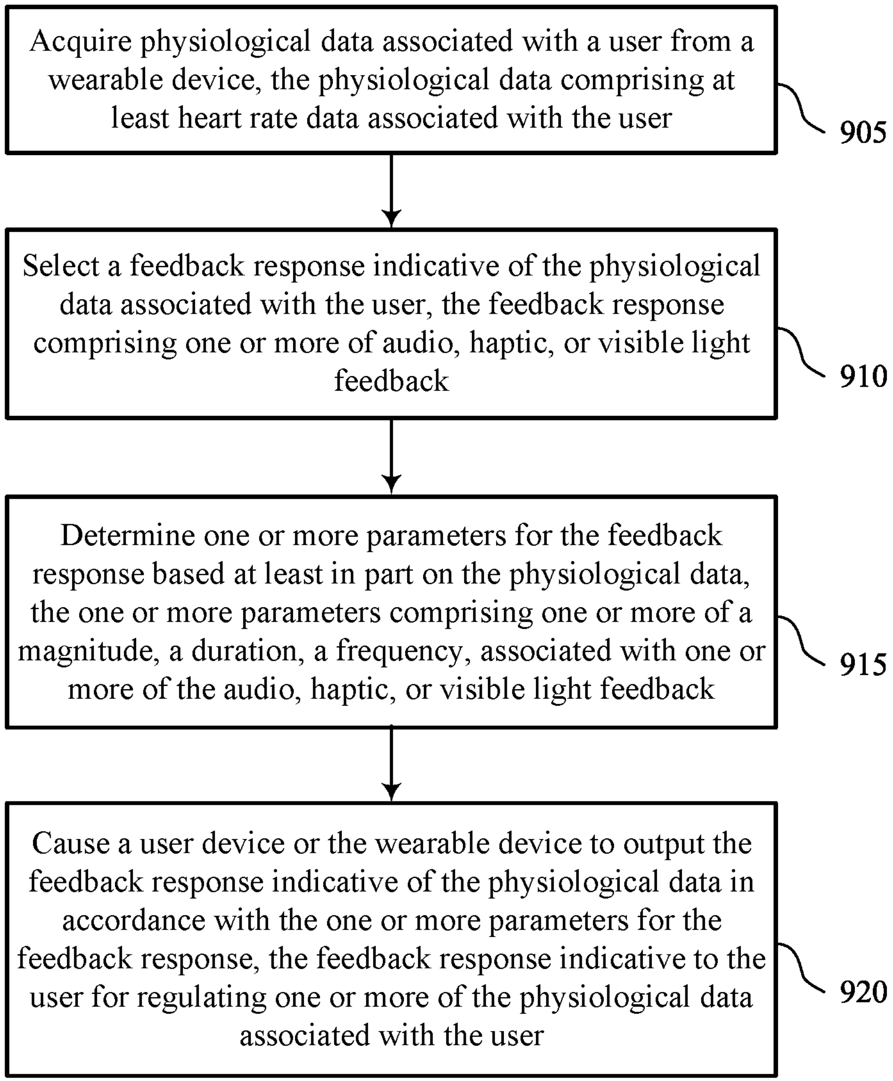
FIGS. 9 through 11 illustrate flowcharts showing methods that support techniques for biofeedback using heart rate data in accordance with aspects of the present disclosure.

FIG. 9 illustrates a flowchart showing a method 900 that supports techniques for biofeedback using heart rate data in accordance with aspects of the present disclosure. The operations of the method 900 may be implemented by a user device or its components as described herein. For example, the operations of the method 900 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 905, the method may include acquiring physiological data associated with a user from a wearable device, the physiological data comprising at least heart rate data associated with the user. The operations of 905 may be performed in accordance with examples as disclosed herein. In some examples, aspects of the operations of 905 may be performed by a data component 725 as described with reference to FIG. 7.

At 910, the method may include selecting a feedback response indicative of the physiological data associated with the user, the feedback response comprising one or more of audio, haptic, or visible light feedback. The operations of 910 may be performed in accordance with examples as disclosed herein. In some examples, aspects of the operations of 910 may be performed by a feedback component 730 as described with reference to FIG. 7.

At 915, the method may include determining one or more parameters for the feedback response based at least in part on the physiological data, the one or more parameters comprising one or more of a magnitude, a duration, or a frequency, associated with one or more of the audio, haptic, or visible light feedback. The operations of 915 may be performed in accordance with examples as disclosed herein. In some examples, aspects of the operations of 915 may be performed by a parameter component 735 as described with reference to FIG. 7.

At 920, the method may include causing a user device or the wearable device to output the feedback response indicative of the physiological data in accordance with the one or more parameters for the feedback response, the feedback response indicative to the user for regulating one or more of the physiological data associated with the user. The operations of 920 may be performed in accordance with examples as disclosed herein. In some examples, aspects of the operations of 920 may be performed by a feedback component 730 as described with reference to FIG. 7.

Figure 10:
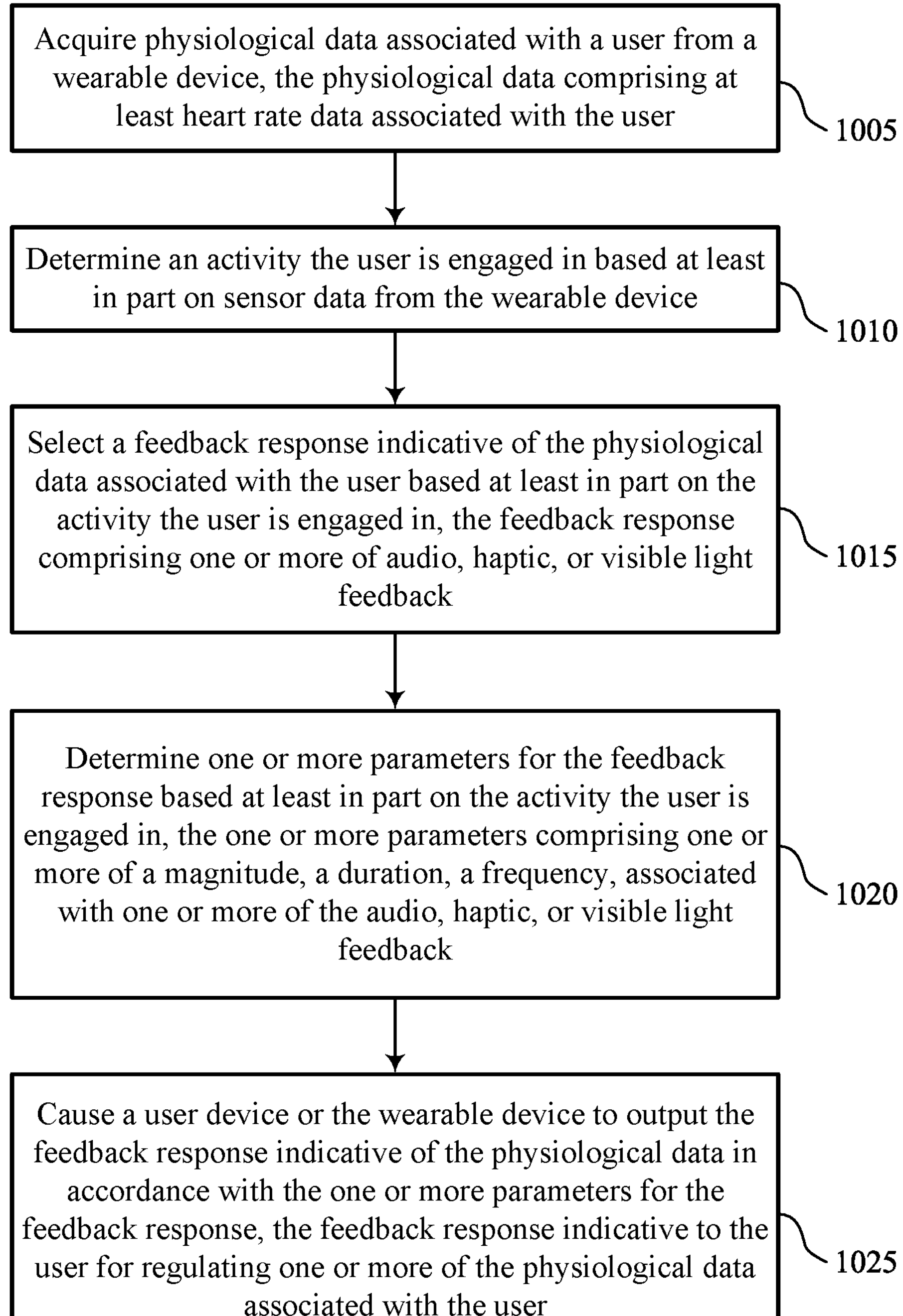

FIG. 10 illustrates a flowchart showing a method 1000 that supports techniques for biofeedback using heart rate data in accordance with aspects of the present disclosure. The operations of the method 1000 may be implemented by a user device or its components as described herein. For example, the operations of the method 1000 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1005, the method may include acquiring physiological data associated with a user from a wearable device, the physiological data comprising at least heart rate data associated with the user. The operations of 1005 may be performed in accordance with examples as disclosed herein. In some examples, aspects of the operations of 1005 may be performed by a data component 725 as described with reference to FIG. 7.

At 1010, the method may include determining an activity the user is engaged in based at least in part on sensor data from the wearable device. The operations of 1010 may be performed in accordance with examples as disclosed herein. In some examples, aspects of the operations of 1010 may be performed by an activity component 740 as described with reference to FIG. 7.

At 1015, the method may include selecting a feedback response indicative of the physiological data associated with the user based at least in part on the activity the user is engaged in, the feedback response comprising one or more of audio, haptic, or visible light feedback. The operations of 1015 may be performed in accordance with examples as disclosed herein. In some examples, aspects of the operations of 1015 may be performed by a feedback component 730 as described with reference to FIG. 7.

At 1020, the method may include determining one or more parameters for the feedback response based at least in part on the activity the user is engaged in, the one or more parameters comprising one or more of a magnitude, a duration, or a frequency, associated with one or more of the audio, haptic, or visible light feedback. The operations of 1020 may be performed in accordance with examples as disclosed herein. In some examples, aspects of the operations of 1020 may be performed by a parameter component 735 as described with reference to FIG. 7.

At 1025, the method may include causing a user device or the wearable device to output the feedback response indicative of the physiological data in accordance with the one or more parameters for the feedback response, the feedback response indicative to the user for regulating one or more of the physiological data associated with the user. The operations of 1025 may be performed in accordance with examples as disclosed herein. In some examples, aspects of the operations of 1025 may be performed by a feedback component 730 as described with reference to FIG. 7.

Figure 11:
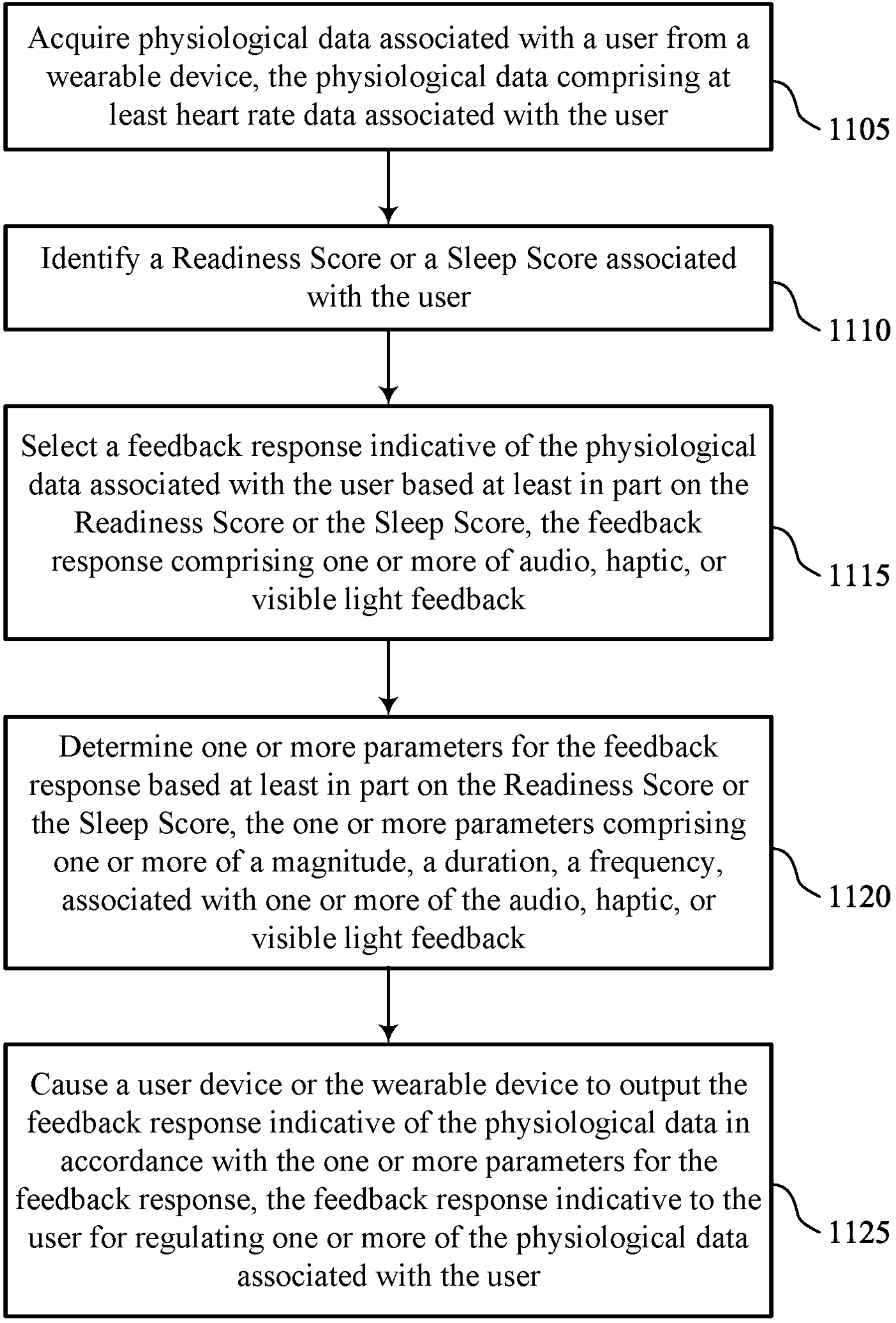

FIG. 11 illustrates a flowchart showing a method 1100 that supports techniques for biofeedback using heart rate data in accordance with aspects of the present disclosure. The operations of the method 1100 may be implemented by a user device or its components as described herein. For example, the operations of the method 1100 may be performed by a user device as described with reference to FIGS. 1 through 8. In some examples, a user device may execute a set of instructions to control the functional elements of the user device to perform the described functions. Additionally, or alternatively, the user device may perform aspects of the described functions using special-purpose hardware.

At 1105, the method may include acquiring physiological data associated with a user from a wearable device, the physiological data comprising at least heart rate data associated with the user. The operations of 1105 may be performed in accordance with examples as disclosed herein. In some examples, aspects of the operations of 1105 may be performed by a data component 725 as described with reference to FIG. 7.

At 1110, the method may include identifying a Readiness Score or a Sleep Score associated with the user. The operations of 1110 may be performed in accordance with examples as disclosed herein. In some examples, aspects of the operations of 1110 may be performed by a score component 745 as described with reference to FIG. 7.

At 1115, the method may include selecting a feedback response indicative of the physiological data associated with the user based at least in part on the Readiness Score or the Sleep Score, the feedback response comprising one or more of audio, haptic, or visible light feedback. The operations of 1115 may be performed in accordance with examples as disclosed herein. In some examples, aspects of the operations of 1115 may be performed by a feedback component 730 as described with reference to FIG. 7.

At 1120, the method may include determining one or more parameters for the feedback response based at least in part on the Readiness Score or the Sleep Score, the one or more parameters comprising one or more of a magnitude, a duration, or a frequency, associated with one or more of the audio, haptic, or visible light feedback. The operations of 1120 may be performed in accordance with examples as disclosed herein. In some examples, aspects of the operations of 1120 may be performed by a parameter component 735 as described with reference to FIG. 7.

At 1125, the method may include causing a user device or the wearable device to output the feedback response indicative of the physiological data in accordance with the one or more parameters for the feedback response, the feedback response indicative to the user for regulating one or more of the physiological data associated with the user. The operations of 1125 may be performed in accordance with examples as disclosed herein. In some examples, aspects of the operations of 1125 may be performed by a feedback component 730 as described with reference to FIG. 7.

It should be noted that the methods described above describe possible implementations, and that the operations and the steps may be rearranged or otherwise modified and that other implementations are possible. Furthermore, aspects from two or more of the methods may be combined.

A method for biofeedback is described. The method may include acquiring physiological data associated with a user from a wearable device, the physiological data comprising at least heart rate data associated with the user, selecting a feedback response indicative of the physiological data associated with the user, the feedback response comprising one or more of audio, haptic, or visible light feedback, determining one or more parameters for the feedback response based at least in part on the physiological data, the one or more parameters comprising one or more of a magnitude, a duration, or a frequency, associated with one or more of the audio, haptic, or visible light feedback, and causing a user device or the wearable device to output the feedback response indicative of the physiological data in accordance with the one or more parameters for the feedback response, the feedback response indicative to the user for regulating one or more of the physiological data associated with the user.

An apparatus for biofeedback is described. The apparatus may include a processor, memory coupled with the processor, and instructions stored in the memory. The instructions may be executable by the processor to cause the apparatus to acquire physiological data associated with a user from a wearable device, the physiological data comprising at least heart rate data associated with the user, select a feedback response indicative of the physiological data associated with the user, the feedback response comprising one or more of audio, haptic, or visible light feedback, determine one or more parameters for the feedback response based at least in part on the physiological data, the one or more parameters comprising one or more of a magnitude, a duration, or a frequency, associated with one or more of the audio, haptic, or visible light feedback, and cause a user device to output the feedback response indicative of the physiological data in accordance with the one or more parameters for the feedback response, the feedback response indicative to the user for regulating one or more of the physiological data associated with the user.

Another apparatus for biofeedback is described. The apparatus may include means for acquiring physiological data associated with a user from a wearable device, the physiological data comprising at least heart rate data associated with the user, means for selecting a feedback response indicative of the physiological data associated with the user, the feedback response comprising one or more of audio, haptic, or visible light feedback, means for determining one or more parameters for the feedback response based at least in part on the physiological data, the one or more parameters comprising one or more of a magnitude, a duration, or a frequency, associated with one or more of the audio, haptic, or visible light feedback, and means for causing a user device or the wearable device to output the feedback response indicative of the physiological data in accordance with the one or more parameters for the feedback response, the feedback response indicative to the user for regulating one or more of the physiological data associated with the user.

A non-transitory computer-readable medium storing code for biofeedback is described. The code may include instructions executable by a processor to acquire physiological data associated with a user from a wearable device, the physiological data comprising at least heart rate data associated with the user, select a feedback response indicative of the physiological data associated with the user, the feedback response comprising one or more of audio, haptic, or visible light feedback, determine one or more parameters for the feedback response based at least in part on the physiological data, the one or more parameters comprising one or more of a magnitude, a duration, or a frequency, associated with one or more of the audio, haptic, or visible light feedback, and cause a user device to output the feedback response indicative of the physiological data in accordance with the one or more parameters for the feedback response, the feedback response indicative to the user for regulating one or more of the physiological data associated with the user.

Some examples of the method, apparatuses, and non-transitory computer-readable medium described herein may further include operations, features, means, or instructions for determining an activity the user may be engaged in based at least in part on sensor data from the wearable device and wherein selecting the feedback response, determining the one or more parameters for the feedback response, or both, may be based at least in part on the activity the user may be engaged in.

Some examples of the method, apparatuses, and non-transitory computer-readable medium described herein may further include operations, features, means, or instructions for identifying a Readiness Score or a Sleep Score associated with the user and wherein selecting the feedback response, determining the one or more parameters for the feedback response, or both, may be based at least in part on the Readiness Score or the Sleep Score associated with the user.

Some examples of the method, apparatuses, and non-transitory computer-readable medium described herein may further include operations, features, means, or instructions for determining a change in one or more physiological data associated with the user after outputting the feedback response indicative of the physiological data to the user, adjusting the feedback response including the one or more parameters for the feedback response based at least in part on the change in the one or more physiological data associated with the user, and causing the user device or the wearable device to output the adjusted feedback response indicative of the change in the one or more physiological data in accordance with the one or more adjusted parameters for the feedback response.

Some examples of the method, apparatuses, and non-transitory computer-readable medium described herein may further include operations, features, means, or instructions for determining a change in an activity the user may be engaged in based at least in part on sensor data from the wearable device, adjusting the feedback response including the one or more parameters for the feedback response based at least in part on the change in the activity the user may be engaged in, and wherein causing the user device or the wearable device to output the adjusted feedback response indicative of the change in the one or more physiological data may be based at least in part on the change in the activity the user may be engaged in.

In some examples of the method, apparatuses, and non-transitory computer-readable medium described herein, adjusting the one or more parameters for the feedback response may include operations, features, means, or instructions for increasing or decreasing one or more of the magnitude, the duration, or the frequency, associated with one or more of the audio, haptic, or visible light feedback.

In some examples of the method, apparatuses, and non-transitory computer-readable medium described herein, outputting the feedback response indicative of the physiological data may include operations, features, means, or instructions for causing an audio interface of the user device to output the audio feedback and causing a GUI of the user device to output the haptic feedback.

Some examples of the method, apparatuses, and non-transitory computer-readable medium described herein may further include operations, features, means, or instructions for pairing the user device with a Bluetooth device, wherein outputting the feedback response indicative of the physiological data comprises, causing the Bluetooth device to output the audio feedback indicative of the physiological data based at least in part on the pairing, and causing the Bluetooth device to output the haptic feedback indicative of the physiological data based at least in part on the pairing.

In some examples of the method, apparatuses, and non-transitory computer-readable medium described herein, causing the user device or the wearable device to output the feedback response indicative of the physiological data may include operations, features, means, or instructions for transmitting a command to the wearable device to cause an interface of the wearable device to output the haptic feedback or the visible light feedback indicative of the physiological data.

Some examples of the method, apparatuses, and non-transitory computer-readable medium described herein may further include operations, features, means, or instructions for receiving second physiological data associated with a second user, the second physiological data comprising second heart rate data associated with the second user, synching the physiological data associated with the user and the second physiological data associated with the second user, and wherein determining the one or more parameters for the feedback response may be based at least in part on the synching.

Some examples of the method, apparatuses, and non-transitory computer-readable medium described herein may further include operations, features, means, or instructions for selecting audio content from a plurality of audio content based at least in part on the physiological data associated with the user, wherein outputting the feedback response indicative of the physiological data comprises, and outputting via the user device the audio content to the user.

Some examples of the method, apparatuses, and non-transitory computer-readable medium described herein may further include operations, features, means, or instructions for determining a heart rate zone based at least in part on the acquired physiological data associated with the user from the wearable device and wherein selecting the feedback response indicative of the physiological data associated with the user may be based at least in part on the heart rate zone.

In some examples of the method, apparatuses, and non-transitory computer-readable medium described herein, the feedback response may be indicative to the user to maintain a heart rate associated with the user within the heart rate zone, or adjust the heart rate associated with the user to switch to a different heart rate zone of a set of heart rate zones associated with the user.

In some examples of the method, apparatuses, and non-transitory computer-readable medium described herein, the set of heart rate zones comprises one or more of a first range of heart rates associated with a first percentage of a maximum heart rate associated with the user, a second range of heart rates associated with a second percentage of the maximum heart rate associated with the user, or a third range of heart rates associated with a third percentage of the maximum heart rate associated with the user, or a combination thereof.

Some examples of the method, apparatuses, and non-transitory computer-readable medium described herein may further include operations, features, means, or instructions for selecting the feedback response indicative of the physiological data associated with the user may be based at least in part on a machine learning model and the machine learning model may be trained to identify relationships between a respective heart rate data and one or more of a respective magnitude, a respective duration, or a respective frequency, associated with one or more of a respective audio, haptic, or visible light feedback.

In some examples of the method, apparatuses, and non-transitory computer-readable medium described herein, one or more of the audio, the haptic, or the visible light feedback may be generated based at least in part on the heart rate data associated with the user, or both.

In some examples of the method, apparatuses, and non-transitory computer-readable medium described herein, the wearable device comprises a wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for biofeedback, comprising:

acquiring physiological data associated with a user from a wearable device that comprises one or more sensors configured to interface with a tissue of the user to measure the physiological data associated with the user, the physiological data comprising at least heart rate data associated with the user;

selecting a feedback response that is based at least in part on the physiological data associated with the user, the feedback response comprising one or more of audio pulses, haptic pulses, or visible light pulses;

determining, in real-time, one or more parameters for the feedback response based at least in part on the physiological data and target physiological data associated with the user, the one or more parameters comprising one or more of a magnitude, a duration, or a frequency, associated with one or more of the audio pulses, the haptic pulses, or the visible light pulses, wherein the one or more parameters are based at least in part on a difference between the physiological data and the target physiological data and the difference is based at least in part on the physiological data being higher or lower than the target physiological data; and transmitting a signal to a user device or the wearable device, the signal configured to cause the user device or the wearable device to output the feedback response in real-time and in accordance with the one or more parameters for the feedback response, the feedback response indicative to the user for regulating one or more parameters of the physiological data associated with the user based at least in part on the target physiological data.

2. The method of claim 1, further comprising:

determining an activity the user is engaged in based at least in part on sensor data from the wearable device, wherein selecting the feedback response, determining the one or more parameters for the feedback response, or both, is based at least in part on the activity the user is engaged in.

3. The method of claim 1, further comprising:

identifying a Readiness Score or a Sleep Score associated with the user, wherein selecting the feedback response, determining the one or more parameters for the feedback response, or both, is based at least in part on the Readiness Score or the Sleep Score associated with the user.

4. The method of claim 1, further comprising:

determining a change in one or more physiological data associated with the user after outputting the feedback response indicative of the physiological data to the user;

adjusting the feedback response including the one or more parameters for the feedback response based at least in part on the change in the one or more physiological data associated with the user; and causing the user device or the wearable device to output the adjusted feedback response indicative of the change in the one or more physiological data in accordance with the one or more adjusted parameters for the feedback response.

5. The method of claim 4, further comprising:

determining a change in an activity the user is engaged in based at least in part on sensor data from the wearable device; and adjusting the feedback response including the one or more parameters for the feedback response based at least in part on the change in the activity the user is engaged in, wherein causing the user device or the wearable device to output the adjusted feedback response indicative of the change in the one or more physiological data is based at least in part on the change in the activity the user is engaged in.

6. The method of claim 5, wherein adjusting the one or more parameters for the feedback response comprises:

increasing or decreasing one or more of the magnitude, the duration, or the frequency, associated with one or more of the audio pulses, the haptic pulses, or the visible light pulses.

7. The method of claim 1, wherein outputting the feedback response indicative of the physiological data comprises:

causing an audio interface of the user device to output the audio pulses; or causing a graphical user interface of the user device to output the haptic pulses.

8. The method of claim 1, further comprising:

pairing the user device with a Bluetooth device, wherein outputting the feedback response indicative of the physiological data comprises:

causing the Bluetooth device to output the audio pulses indicative of the physiological data based at least in part on the pairing;

causing the Bluetooth device to output the haptic pulses indicative of the physiological data based at least in part on the pairing; or causing the Bluetooth device to output the visible light pulses indicative of the physiological data based at least in part on the pairing.

9. The method of claim 1, wherein causing the user device or the wearable device to output the feedback response indicative of the physiological data comprises:

transmitting a command to the wearable device to cause an interface of the wearable device to output the haptic pulses or the visible light pulses indicative of the physiological data.

10. The method of claim 1, further comprising:

receiving second physiological data associated with a second user, the second physiological data comprising second heart rate data associated with the second user; and synching the physiological data associated with the user and the second physiological data associated with the second user, the synching comprising selecting a target heart rate based at least in part on the physiological data associated with the user and the second physiological data associated with the second user, wherein determining the one or more parameters for the feedback response is based at least in part on the synching.

11. The method of claim 1, further comprising:

selecting audio content from a plurality of audio content based at least in part on the physiological data associated with the user, wherein outputting the feedback response indicative of the physiological data comprises:

outputting via the user device the audio content to the user.

12. The method of claim 1, further comprising:

determining a heart rate zone based at least in part on the acquired physiological data associated with the user from the wearable device, wherein selecting the feedback response indicative of the physiological data associated with the user is based at least in part on the heart rate zone.

13. The method of claim 12, wherein the feedback response is indicative to the user to maintain a heart rate associated with the user within the heart rate zone, or adjust the heart rate associated with the user to switch to a different heart rate zone of a set of heart rate zones associated with the user.

14. The method of claim 13, wherein the set of heart rate zones comprises one or more of a first range of heart rates associated with a first percentage of a maximum heart rate associated with the user, a second range of heart rates associated with a second percentage of the maximum heart rate associated with the user, or a third range of heart rates associated with a third percentage of the maximum heart rate associated with the user, or a combination thereof.

15. The method of claim 1, wherein selecting the feedback response indicative of the physiological data associated with the user is based at least in part on a machine learning model, and wherein the machine learning model is trained to identify relationships between a respective heart rate data and one or more of a respective magnitude, a respective duration, or a respective frequency, or a combination thereof associated with one or more of a respective audio, haptic, or visible light feedback.

16. The method of claim 1, wherein one or more of the audio pulses, the haptic pulses, or the visible light pulses are generated based at least in part on the heart rate data associated with the user, or both.

17. The method of claim 1, wherein the wearable device comprises a wearable ring device.

18. An apparatus for biofeedback, comprising:

a processor;

memory coupled with the processor; and instructions stored in the memory and executable by the processor to cause the apparatus to:

acquire physiological data associated with a user from a wearable device that comprises one or more sensors configured to interface with a tissue of the user to measure the physiological data associated with the user, the physiological data comprising at least heart rate data associated with the user;

select a feedback response that is based at least in part on the physiological data associated with the user, the feedback response comprising one or more of audio pulses, haptic pulses, or visible light pulses;

determine, in real-time, one or more parameters for the feedback response based at least in part on the physiological data and target physiological data associated with the user, the one or more parameters comprising one or more of a magnitude, a duration, or a frequency, associated with one or more of the audio pulses, the haptic pulses, or the visible light pulses, wherein the one or more parameters are based at least in part on a difference between the physiological data and the target physiological data and the difference is based at least in part on the physiological data being higher or lower than the target physiological data; and transmit a signal to a user device or the wearable device, the signal configured to cause the user device or the wearable device to output the feedback response in real-time and in accordance with the one or more parameters for the feedback response, the feedback response indicative to the user for regulating one or more parameters of the physiological data associated with the user based at least in part on the target physiological data.

19. The apparatus of claim 18, wherein the instructions are further executable by the processor to cause the apparatus to:

determine an activity the user is engaged in based at least in part on sensor data from the wearable device, wherein to select the feedback response, determine the one or more parameters for the feedback response, or both, is based at least in part on the activity the user is engaged in.

20. A non-transitory computer-readable medium storing code for biofeedback, the code comprising instructions executable by a processor to:

acquire physiological data associated with a user from a wearable device that comprises one or more sensors configured to interface with a tissue of the user to measure the physiological data associated with the user, the physiological data comprising at least heart rate data associated with the user;

select a feedback response that is based at least in part on the physiological data associated with the user, the feedback response comprising one or more of audio pulses, haptic pulses, or visible light pulses;

determine, in real-time, one or more parameters for the feedback response based at least in part on the physiological data and target physiological data associated with the user, the one or more parameters comprising one or more of a magnitude, a duration, or a frequency, associated with one or more of the audio pulses, the haptic pulses, or the visible light pulses, wherein the one or more parameters are based at least in part on a difference between the physiological data and the target physiological data and the difference is based at least in part on the physiological data being higher or lower than the target physiological data; and transmit a signal to a user device or the wearable device, the signal configured to cause the user device or the wearable device to output the feedback response in real-time and in accordance with the one or more parameters for the feedback response, the feedback response indicative to the user for regulating one or more parameters of the physiological data associated with the user based at least in part on the target physiological data.

* * * * *